US009683980B1

(12) United States Patent
Basheer et al.

(10) Patent No.: US 9,683,980 B1
(45) Date of Patent: Jun. 20, 2017

(54) METHOD FOR DETECTING HG²⁺ IN AN AQUEOUS SOLUTION

(71) Applicant: KING FAHD UNIVERSITY OF PETROLEUM AND MINERALS, Dhahran (SA)

(72) Inventors: Chanbasha Basheer, Tamil Nadu (IN); Salawu Omobayo Adio, Kaduna (NG)

(73) Assignee: KING FAHD UNIVERSITY OF PETROLEUM AND MINERALS, Dhahran (SA)

( * ) Notice: Subject to any disclaimer, the term of this patent is extended or adjusted under 35 U.S.C. 154(b) by 0 days.

(21) Appl. No.: 15/060,238

(22) Filed: Mar. 3, 2016

(51) Int. Cl.
*G01N 21/78* (2006.01)
*G01N 31/22* (2006.01)
*G01N 33/18* (2006.01)
*G01N 33/20* (2006.01)
*G01N 33/84* (2006.01)

(52) U.S. Cl.
CPC ......... *G01N 33/1813* (2013.01); *G01N 21/78* (2013.01); *G01N 31/22* (2013.01); *G01N 33/84* (2013.01); *G01N 33/1826* (2013.01); *G01N 33/20* (2013.01)

(58) Field of Classification Search
CPC .... G01N 21/77; G01N 21/78; G01N 33/0098; G01N 33/18; G01N 33/1813; G01N 33/1826; G01N 33/20; G01N 31/22; Y10T 436/25
USPC .. 436/73, 74, 79, 80, 81, 84, 164, 166, 171, 436/174
See application file for complete search history.

(56) References Cited

U.S. PATENT DOCUMENTS 9,491,947 B1 * 11/2016 Awad ................. A01N 59/16
2010/0200501 A1 * 8/2010 Hoag .................. B22F 1/0018
                                                       210/620

FOREIGN PATENT DOCUMENTS

WO       2005/095031 A1    10/2005

OTHER PUBLICATIONS

Kumar et al. Spectrochimica Acta Part A: Molecular and Biomolecular Spectroscopy, vol. 129, Mar. 24, 2014, pp. 35-42.*
Ahmed et al. Journal of Photochemistry and Photobiology B: Biology, vol. 151, Jul. 3, 2015, pp. 39-45.*
Alam et al. Spectrochimica Acta Part A: Molecular and Biomolecular Spectroscopy, vol. 137, Sep. 8, 2014, pp. 503-508.*
Farhadi, K., et al., "Highly Selective Hg2+ Colorimetric Sensor using Green Synthesized and Unmodified Silver Nanoparticles", Sensors and Actuators B: Chemical, 6 Pages total, (2011).
Jayapriya, E., et al., "Synthesis of Silver Nanoparticles using Leaf Aqueous Extract of *Ocimum basilicum* (L.)", International Journal of Chemtech Research, vol. 5, No. 6, pp. 2985-2992, (2013).
Khalil, M.M.H., et al., "Green Synthesis of Silver Nanoparticles using Olive Leaf Extract and its Antibacterial Activity", Arabian Journal of Chemistry, vol. 7, pp. 1131-1139, (2014).
Vanaja, M., et al.. "Phytosynthesis of Silver Nanoparticles by Cissus Quadrangularis: Influence of Physicochemical Factors", Journal of Nanostructure in Chemistry, vol. 3, No. 17, 8 Pages total, (2013).
Ahmed, S., et al., "A Review on Plants Extract Mediated Synthesis of Silver Nanoparticles for Antimicrobial Applications: A Green Expertise", Journal of Advanced Research, 12 Pages total, (2015).
Jain, N., et al., "Removal of Protein Capping Enhances the Antibacterial Efficiency of Biosynthesized Silver Nanoparticles", PLOS One, vol. 10, No. 7, 19 Pages total, (Jul. 30, 2015).
Irwin, P., et al., "Antimicrobial Activity of Spherical Silver Nanoparticles Prepared using a Biocompatible Macromolecular Capping Agent: Evidence for Induction of a Greatly Prolonged Bacterial Lag Phase", Journal of Nanobiotechnology, vol. 8, No. 34, 12 Pages total, (2010).
Ahmad, N., et al., "Rapid Synthesis of Silver Nanoparticles using Dried Medicinal Plant of Basil", Colloids and Surfaces B: Biointerfaces, vol. 81, No. 1, 2 Pages total, (Nov. 1, 2010) (Abstract only).

* cited by examiner

*Primary Examiner* — Maureen Wallenhorst
(74) *Attorney, Agent, or Firm* — Oblon, McClelland, Maier & Neustadt, L.L.P.

(57) ABSTRACT

A method of detecting $Hg^{2+}$ in an aqueous solution. The method includes contacting the aqueous solution with a composition containing a plant extract and biosynthesized silver nanoparticles. The composition has an average particle size of 30-50 nm. A color change following the contacting indicates the presence of $Hg^{2+}$ in the aqueous solution. The composition is preferably synthesized by reduction of a silver salt with an extract of *Ocimum basilicum*.

20 Claims, 24 Drawing Sheets

METHOD FOR DETECTING HG$^{2+}$ IN AN AQUEOUS SOLUTION

BACKGROUND OF THE INVENTION

Technical Field

The present disclosure relates to methods for detecting Hg$^{2+}$ in an aqueous solution. More specifically, the present disclosure relates to colorimetric methods for detecting Hg$^{2+}$ in an aqueous solution with a composition comprising a plant extract and biosynthesized silver nanoparticles.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, is neither expressly nor impliedly admitted as prior art against the present invention.

Mercury is considered to be one of the most dangerous metal ions in the environment, posing severe health risks to humans, because mercury is widely distributed in air, water and soil in metallic, inorganic, and organic forms. Mercuric ion (Hg$^{2+}$), the most stable form of inorganic mercury, exists mostly in surface water due to its high water solubility. People exposed to Hg$^{2+}$ suffer from developmental delays and other health problems due to damages to the brain, nervous system, kidneys, and the endocrine system. Therefore, it is critical to be able to detect and measure the level of Hg$^{2+}$ in both environmental and biological samples under aqueous conditions with high sensitivity and selectivity and without interference of other metal ions.

There are various classical methods for mercury detection, including atomic absorption/emission spectrometry (AAS/AES), inductively coupled plasma mass spectrometry (ICPMS), atomic fluorescence spectrometry (AFS), high-performance liquid chromatography (HPLC), ion selective electrode (ISE), and flame photometry. Although all of the above methods are powerful techniques for the determination of Hg$^{2+}$, their excellent performance requires expensive instrumentation and time-consuming sample preparation and preconcentration procedures.

It is thus an object of the present disclosure to provide a simple and economical, and yet sensitive and selective colorimetric method of detecting Hg$^{2+}$ in an aqueous solution with a composition comprising a plant extract and biosynthesized silver nanoparticles.

BRIEF SUMMARY OF THE INVENTION

The present disclosure relates to a method of detecting Hg$^{2+}$ in an aqueous solution. The method includes contacting the aqueous solution with a composition comprising a plant extract and biosynthesized silver nanoparticles. The composition has an average particle size of 30-50 nm. A color change following the contacting indicates the presence of Hg$^{2+}$ in the aqueous solution.

In one or more embodiments, the plant extract comprises at least one selected from the group consisting of alkaloids, flavonoids, saponins, carbohydrates, polysaccharides, terpenoids, steroids, sterols, phenols, tannins, anthraquinones, anthocyanins, amino acids, proteins, and vitamins.

In one or more embodiments, the composition is of uniform shape.

In one or more embodiments, the uniform shape is selected from the group consisting of a spherical shape, a triangular shape, a rod shape, and a cubic shape.

In one or more embodiments, the color change is detected and quantified by a decrease in absorbance at a wavelength of 380-450 nm by UV-visible spectrophotometry.

In one or more embodiments, the magnitude of the color change detected by the UV-visible spectrophotometry linearly correlates with the concentration of Hg$^{2+}$ in the aqueous solution ranging from about 1 µM to 90 µM.

In one or more embodiments, the color change detected and quantified by the UV-visible spectrophotometry correlates with a concentration of Hg$^{2+}$ in the aqueous solution, and a lowest concentration of Hg$^{2+}$ in the aqueous solution detected by the UV-visible spectrophotometry is about 40-200 nM.

In one or more embodiments, the aqueous solution further comprises at least one metal cation selected from of the group consisting of Ca$^{2+}$, Cu$^{2+}$, Mn$^{2+}$, Ni$^{2+}$, Na$^{2+}$, Zn$^{2+}$, Ba$^{2+}$, and K$^+$.

In one or more embodiments, the composition is synthesized by reduction of a silver salt with an extract of *Ocimum basilicum*.

In one or more embodiments, the reduction of the silver salt with the extract of *Ocimum basilicum* comprises mixing an aqueous solution of the silver salt with an aqueous extract of *Ocimum basilicum* and reducing the silver salt with the aqueous extract of *Ocimum basilicum* for a period of at least 120 minutes to form a biosynthesized silver nanoparticle mixture.

In one or more embodiments, the reduction of the silver salt with the extract of *Ocimum basilicum* comprises mixing an aqueous solution of the silver salt with an aqueous extract of *Ocimum basilicum* and reducing the silver salt with the aqueous extract of *Ocimum basilicum* in a temperature range of 20-75° C. to form a biosynthesized silver nanoparticle mixture.

In one or more embodiments, the reduction of the silver salt with the extract of *Ocimum basilicum* comprises mixing an aqueous solution of the silver salt with an aqueous extract of *Ocimum basilicum* to form a reaction mixture with a pH of 7-12 and reducing the silver salt with the aqueous extract of *Ocimum basilicum* to form a biosynthesized silver nanoparticle mixture.

In one or more embodiments, the reduction of the silver salt with the extract of *Ocimum basilicum* comprises mixing an aqueous solution of the silver salt with an aqueous extract of *Ocimum basilicum* and reducing the silver salt with the aqueous extract of *Ocimum basilicum* to form a biosynthesized silver nanoparticle mixture. The concentration of the silver salt in the aqueous solution of the silver salt is about 1-5 mM, and the volume ratio of the aqueous extract of *Ocimum basilicum* to the aqueous solution of the silver salt is no greater than 1:1.

In one or more embodiments, the reduction of the silver salt with the extract of *Ocimum basilicum* comprises mixing an aqueous solution of the silver salt with an aqueous extract of *Ocimum basilicum* and reducing the silver salt with an effective amount of the aqueous extract of *Ocimum basilicum* to form a biosynthesized silver nanoparticle mixture. The aqueous extract of *Ocimum basilicum* is produced by boiling at least one leaf, or a part thereof, of *Ocimum basilicum* in water, and the ratio of the weight of the at least one leaf, or a part thereof, of *Ocimum basilicum* to the volume of the water is about 3-30 g of the at least one leaf, or a part thereof, of *Ocimum basilicum* per 100 ml of the water.

In one or more embodiments, the effective amount of the aqueous extract of *Ocimum basilicum* corresponds to a volume ratio of the aqueous extract of *Ocimum basilicum* to the aqueous solution of the silver salt in the range of about 1:20-1:75.

In one or more embodiments, the extract of *Ocimum basilicum* is obtained from at least one part of *Ocimum basilicum* selected from the group consisting of a leaf, a flower, a stem, and a root.

In one or more embodiments, the silver salt comprises at least one selected from the group consisting of silver halide, silver sulfate, and silver nitrate.

In one or more embodiments, the reduction of a silver salt with an extract of *Ocimum basilicum* comprises mixing an aqueous solution of the silver salt with an aqueous extract of *Ocimum basilicum* to form a reaction mixture with a pH of 9-11 and reducing the silver salt with the aqueous extract of *Ocimum basilicum* for 120-240 minutes and at a temperature of 20-75° C. to form a biosynthesized silver nanoparticle mixture. The concentration of the silver salt in the aqueous solution of the silver salt is about 1-3 mM, and the volume ratio of the aqueous extract of *Ocimum basilicum* to the aqueous solution of the silver salt is in the range of about 1:20-1:75.

In one or more embodiments, the reduction of a silver salt with an extract of *Ocimum basilicum* further comprises separating the composition from the biosynthesized silver nanoparticle mixture.

In one or more embodiments, the reduction of the silver salt with the extract of *Ocimum basilicum* comprises mixing an aqueous solution of the silver salt with an aqueous extract of *Ocimum basilicum* to form a reaction mixture and reducing the silver salt with the aqueous extract of *Ocimum basilicum* to form a biosynthesized silver nanoparticle mixture. The average particle size and shape of the composition are determined by the pH of the reaction mixture, the duration and the temperature of the reducing, the concentration of the silver salt and the concentration of the aqueous extract of *Ocimum basilicum* in the reaction mixture, the parts of *Ocimum basilicum* used to make the aqueous extract of *Ocimum basilicum*, and the type of *Ocimum basilicum* used.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
FIG. 1 is a picture showing *Ocimum basilicum* with the leaves and flowers according to Example 1.

Disclosed herein is a method of detecting $Hg^{2+}$ in an aqueous solution. The method includes contacting the aqueous solution with a composition comprising a plant extract and biosynthesized silver nanoparticles. The composition has an average particle size of 30-50 nm. A color change following the contacting indicates the presence of $Hg^{2+}$ in the aqueous solution.

The disclosed method can be used in detecting $Hg^{2+}$ present in various types of water. In some embodiments, the aqueous solution comprises at least one selected from the group consisting of waste water, tap water, river water, lake water, ground water, and drinking water. In other embodiments, the aqueous solution comprises water that has been contacted with at least one water-soluble and/or water-insoluble substance which contains or may contain, or which is adsorbed with or may be absorbed with $Hg^{2+}$. Examples of the substance, without limitation, include lake sediments and soil.

The disclosed method may also be used to detect $Hg^{2+}$ from various biological samples, such as whole blood, plasma, serum, saliva, sweat, urine, washes of tissues, extracts of tissues, amniotic fluid, placental fluid, and pharmaceutical and dietary compositions that may be contaminated with $Hg^{2+}$. $Hg^{2+}$ from non-aqueous biological samples or pharmaceutical and dietary compositions may be first extracted with water or a suitable aqueous solution, such as a phosphate buffered saline solution, with the resulting $Hg^{2+}$ containing extract being optionally diluted, before the $Hg^{2+}$ is detected and quantified by the disclosed method.

Silver nanoparticles with a well-controlled particle size exhibit color changes when interacting with certain adsorbed substances, including $Hg^{2+}$, due to light-excited surface plasmon resonance vibrations that are dependent on a number of parameters, such as the average particle size and shape of the silver nanoparticles, the adsorbed substances, the dielectric properties of the medium, and the distance between the silver nanoparticles. The particle size of silver nanoparticles is considered to be well-controlled when the particle size distribution of silver nanoparticles is such that the percentage of silver nanoparticles having a particle size that is greater than 3 standard deviations different from the average particle size of the entire silver nanoparticle population is less than 10%, or preferably less than 5%, or more preferably less than 1%. As a result, silver nanoparticles of an appropriate average particle size and shape allow for sensitive detection of $Hg^{2+}$ in an aqueous solution, even with the naked eye at certain $Hg^{2+}$ concentrations and detection conditions. Additionally, silver nanoparticles are photostable and do not undergo photobleaching, making silver nanoparticles even more suitable as a colorimetric sensor for $Hg^{2+}$ detection.

Conventional methods of synthesizing silver nanoparticles include physical and chemical methods. Chemical methods for the preparation of silver nanoparticles include borohydride and citrate reduction methods. Physical methods include vapor deposition, lithographic processes and molecular beam epitaxy (MBE). Reduction of $Ag^+$ by radiolysis is also frequently used for the preparation of silver nanoparticles. These methods sometimes require the use of toxic chemicals dangerous both to humans and the environment. Additionally, the silver nanoparticles prepared by the chemical methods most often agglomerate to form big particles and need to be further modified with supplementary stabilizing agents, or capping agents, to restrict agglomeration of the silver nanoparticles to increase their detection sensitivity for $Hg^{2+}$, for example.

Silver nanoparticles can also be prepared by biosynthesis using fungi, bacteria, or preferably plant extracts that contain phytochemicals and/or metabolites capable of reducing a silver salt, which is preferably dissolved in an aqueous solution, to silver nanoparticles, and capable of stabilizing the silver nanoparticles formed. Compared with the chemical methods, biosynthesis of silver nanoparticles with a plant extract provides a more efficient synthetic pathway through a one-step process without the use of supplementary surfactants or polymers, capping agents, or templates to restrict agglomeration of the silver nanoparticles, since some of the phytochemicals and/or metabolites present in the plant extract perform dual roles as both a reducing agent for the silver salt and as a stabilizer forming a sturdy coating on the silver nanoparticles to control agglomeration of the silver nanoparticles.

In some embodiments, the plant extract comprises phytochemicals and/or metabolites that include, without limitation, alkaloids, flavonoids, saponins, carbohydrates, polysaccharides, terpenoids, steroids, sterols, phenols, tannins, anthraquinones, anthocyanins, amino acids, proteins, and vitamins. In some embodiments, the composition comprises a plant extract and biosynthesized silver nanoparticles, with the biosynthesized silver nanoparticles covered with, adsorbed with, and/or attached to the components (e.g. phytochemicals and/or metabolites) of the plant extract, or a portion thereof. In other embodiments, the composition comprises a plant extract and biosynthesized silver nanoparticles, with the biosynthesized silver nanoparticles bonded with the components (e.g. phytochemicals and/or metabolites) of the plant extract, or a portion thereof, through the functional groups of the plant extract components. Non-limiting examples of the functional groups include a carboxyl group, a carbonyl group, an amine group, a hydroxyl group, and an alkene group.

In a preferred embodiment, the composition is synthesized by reduction of a silver salt with an extract of *Ocimum basilicum*, preferably a leaf extract, preferable a flower extract, or preferably a mixed leaf and flower extract of *Ocimum basilicum*, preferably without any additional, or supplementary, modifications. *Ocimum basilicum* is also known as sweet basil and King of spices. It is a popular Chinese medicinal herb of the family Labiatae. There are thousands of *Ocimum basilicum* available which are classified based on plant morphology, pigmentation, and chemical composition of the essential oils. The whole plant materials and essential oils have been used extensively in food, perfumes, and dental and oral products. Further, the leaves and flowers of *Ocimum basilicum* are administered orally for the treatment of fever, poor digestion, nausea, depression and exhaustion.

In one embodiment, the leaf extract of *Ocimum basilicum* comprises alkaloids, flavonoids, saponins, carbohydrates, terpenoids, sterols, phenols, tannins, anthraquinones, anthocyanins, amino acids and proteins, as disclosed by E. Jayapriya and P. Lalitha, Synthesis of Silver Nanoparticles using Leaf Aqueous Extract of *Ocimum basilicum* (L.), International Journal of ChemTech Research, Vol. 5, No. 6, pp 2985-2992, October-December 2013, and incorporated herein by reference in its entirety. In some embodiments, at least one of the above components of the leaf extract of *Ocimum basilicum* covers, adsorbs on the surface of, and/or bonds with the biosynthesized silver nanoparticles.

In another embodiment, the composition may be synthesized by reduction of a silver salt with an extract of at least one other species of the *Ocimum* genus. Non-limiting examples of the other species of the *Ocimum* genus include *Ocimum africanum, Ocimum americanum, Ocimum amicorum, Ocimum angustifolium, Ocimum burchellianum, Ocimum campechianum, Ocimum canescens, Ocimum carnosum, Ocimum centraliafricanum, Ocimum circinatum, Ocimum coddii, Ocimum cufodontii, Ocimum dambicola, Ocimum decumbens, Ocimum dhofarense, Ocimum dolomiticola, Ocimum ellenbeckii, Ocimum empetroides, Ocimum ericoides, Ocimum filamentosum, Ocimum fimbriatum, Ocimum fischeri, Ocimum formosum, Ocimum forskoelei, Ocimum fruticosum, Ocimum grandiflorum, Ocimum gratissimum, Ocimum hirsutissimum, Ocimum irvinei, Ocimum jamesii, Ocimum kenyense, Ocimum kilimandscharicum, Ocimum labiatum, Ocimum lamiifolium, Ocimum masaiense, Ocimum mearnsii, Ocimum metallorum, Ocimum minimum, Ocimum minutiflorum, Ocimum mitwabense, Ocimum monocotyloides, Ocimum motjaneanum, Ocimum natalense, Ocimum nudicaule, Ocimum nummularia, Ocimum obovatum, Ocimum ovatum, Ocimum pseudoserratum, Ocimum pyramidatum, Ocimum reclinatum, Ocimum serpyllifolium, Ocimum serratum, Ocimum somaliense, Ocimum spectabile, Ocimum spicatum, Ocimum tenuiflorum, Ocimum transamazonicum, Ocimum tubiforme, Ocimum urundense, Ocimum vandenbrandei, Ocimum vanderystii, Ocimum viphyense,* and *Ocimum waterbergense*. In still another embodiment, the composition is synthesized by reduction of a silver salt with a mixed extract of *Ocimum basilicum* and at least one other species of the *Ocimum* genus.

In some embodiments, the reduction of a silver salt with an extract of *Ocimum basilicum* comprises mixing an aqueous solution of the silver salt with an aqueous extract of *Ocimum basilicum* and reducing the silver salt with the aqueous extract of *Ocimum basilicum*, preferably in the dark, for a period of at least 30 minutes, at least 60 minutes, preferably at least 90 minutes, more preferably at least 120 minutes, more preferably at least 180 minutes, more preferably at least 240 minutes, more preferably at least 300 minutes, more preferably at least 360 minutes, or more preferably at least 480 minutes, to form a biosynthesized silver nanoparticle mixture. In this and the following embodiments, the biosynthesized silver nanoparticle mixture comprises the composition comprising biosynthesized silver nanoparticles covered with, adsorbed with, attached to, and/or bonded with the components (e.g. phytochemicals and/or metabolites) from the aqueous extract of *Ocimum basilicum*. Some of the components, such as capping proteins (described in detail below), control or restrict agglomeration of the biosynthesized silver nanoparticles to keep them stable. Some of the components may be phytochemicals and/or metabolites responsible for reducing the silver salt to form the biosynthesized silver nanoparticles, in oxidized (reacted) forms and/or unreacted forms. The biosynthesized silver nanoparticle mixture may also comprise a portion of the aqueous extract of *Ocimum basilicum* that is not associated with the biosynthesized silver nanoparticles and/or unreacted silver salt.

In some embodiments, the reduction of a silver salt with an extract of *Ocimum basilicum* comprises mixing an aqueous solution of the silver salt with an aqueous extract of *Ocimum basilicum* and reducing the silver salt with the aqueous extract of *Ocimum basilicum* in a temperature range of 5-100° C., 10-90° C., 15-80° C., preferably 20-75° C., preferably 25-60° C., or preferably 30-50° C., to form a biosynthesized silver nanoparticle mixture.

In some embodiments, the reduction of a silver salt with an extract of *Ocimum basilicum* comprises mixing an aqueous solution of the silver salt with an aqueous extract of *Ocimum basilicum* to form a reaction mixture with a pH of 6-14, 8-13, preferably 7-12, preferably 7-10, or preferably 8-10, and reducing the silver salt with the aqueous extract of *Ocimum basilicum* to form a biosynthesized silver nanoparticle mixture.

In some embodiments, the reduction of a silver salt with an extract of *Ocimum basilicum* comprises mixing an aqueous solution of the silver salt with an aqueous extract of *Ocimum basilicum* and reducing the silver salt with the aqueous extract of *Ocimum basilicum* to form a biosynthesized silver nanoparticle mixture. The concentration of the silver salt in the aqueous solution of the silver salt is about 0.5-10 mM, about 1-8 mM, or preferably 1-5 mM, or more preferably 1-3 mM. The volume ratio of the aqueous extract of *Ocimum basilicum* to the aqueous solution of the silver salt is no greater than 5:1, or no greater than 2:1, or no greater than 1:1, or no greater than 0.5:1, or no greater than 0.1:1.

In some embodiments, the reduction of a silver salt with an extract of *Ocimum basilicum* comprises mixing an aqueous solution of the silver salt with an aqueous extract of *Ocimum basilicum* and reducing the silver salt with an effective amount of the aqueous extract of *Ocimum basilicum* to form a biosynthesized silver nanoparticle mixture. The aqueous extract of *Ocimum basilicum* is produced by boiling at least one leaf, or a part thereof, of *Ocimum basilicum*, which preferably has been thoroughly washed and finely cut, in water, preferably sterile distilled water, for 1-10 minutes, preferably 2-8 minutes, or more preferably 3-6 minutes, or more preferably 2 minutes. The ratio of the weight of the at least one leaf, or a part thereof, of *Ocimum basilicum* to the volume of the water is about 3-30 g of the at least one leaf, or a part thereof, of *Ocimum basilicum* per 100 ml of the water, about 5-25 g of the at least one leaf, or a part thereof, of *Ocimum basilicum* per 100 ml of the water, about 10-20 g of the at least one leaf, or a part thereof, of *Ocimum basilicum* per 100 ml of the water, or about 12-15 g of the at least one leaf, or a part thereof, of *Ocimum basilicum* per 100 ml of the water. The resulting aqueous (leaf) extract of *Ocimum basilicum* is then preferably filtered. In some embodiments, the effective amount of the aqueous extract of *Ocimum basilicum* corresponds to a volume ratio of the aqueous extract of *Ocimum basilicum* to the aqueous solution of the silver salt in the range of about 1:1-1:200, about 1:10-1:150, preferably about 1:20-1:100, more preferably about 1:20-1:75, or more preferably about 1:25-1:50.

In the above mentioned embodiments, the reduction of the silver salt by the aqueous extract of *Ocimum basilicum* may be monitored using UV-visible spectrophotometry at a wavelength where the composition in the reaction mixture exhibit a peak absorbance. The peak absorbance wavelength may be 380-500 nm, or 400-480 nm, or 400-450 nm, or 400-420 nm, or 420-450 nm. The peak absorbance wavelength may indicate the average particle size of the composition, with an increase in the peak absorbance wavelength correlating with an increase in the average particle size of the composition.

In some embodiments, the extract of *Ocimum basilicum* is obtained from one or more parts of *Ocimum basilicum*. Non-limiting examples of the one or more parts of *Ocimum basilicum* include a leaf, a flower, a stem, and a root.

The *Ocimum basilicum* used to make the extract may be at any growth stage, e.g. at a flowering stage when the flower and/or one or more non-flower parts (e.g. leaf, stem, and root) may be used to make the extract, or alternatively, at a non-flowering stage, when one or more non-flower parts may be used to make the extract.

To make the extract of *Ocimum basilicum*, in one embodiment, the part(s) of *Ocimum basilicum* of interest are collected, washed thoroughly, preferably twice/thrice with tap water, to remove both epiphytes and necrotic plants; preferably followed with sterile distilled water to remove associated debris if any. The clean and fresh plant parts are sun-dried or shade-dried for 5-25 days, or preferably 7-20 days, or more preferably 10-15 days, and then finely cut, or preferably powdered using, for example, a domestic blender. For the plant extract preparation, the dried finely cut or powdered plant parts are boiled, preferably in deionized distilled water (hot percolation method), with the ratios of the weight of the plant parts to the volume of the deionized distilled water being the same as or similar to those described above for making the leaf extract of *Ocimum basilicum*, or with other ratios a person of ordinary skill in the art is capable of determining. The resulting infusion is then preferably filtered thoroughly until no insoluble material appears in the extract. In another embodiment, a solvent other than water, e.g. a mixture of ethyl acetate and methanol, may be used to make the plant extract.

In some embodiments, the silver salt comprises at least one selected from the group consisting of silver halide, silver sulfate, and silver nitrate. In a preferred embodiment, the silver salt is silver nitrate.

In a preferred embodiment, the reduction of a silver salt with an extract of *Ocimum basilicum* comprises mixing an aqueous solution of the silver salt with an aqueous extract of *Ocimum basilicum* to form a reaction mixture with a pH of 9-11 and reducing the silver salt with the aqueous extract of *Ocimum basilicum* for 120-240 minutes and at a temperature of 20-75° C. to form a biosynthesized silver nanoparticle mixture. The concentration of the silver salt in the aqueous solution of the silver salt is about 1-3 mM. The volume ratio of the aqueous extract of *Ocimum basilicum* to the aqueous solution of the silver salt is in the range of about 1:20-1:75. In some embodiments, the composition may be separated from the biosynthesized silver nanoparticle mixture by, for example, conventional methods, such as filtration, or preferably, centrifugation. For example, the biosynthesized silver nanoparticle mixture may be centrifuged at 10,000-17,000 rpm for 5-30 minutes, or for 10-20 minutes, at room temperature. In other embodiments, the composition separated from the biosynthesized silver nanoparticle mixture may be re-dispersed in water, preferably distilled water, or more preferably double distilled water.

In some embodiments, the reduction of a silver salt with an extract of *Ocimum basilicum* comprises mixing an aqueous solution of the silver salt with an aqueous extract of *Ocimum basilicum* to form a reaction mixture and reducing the silver salt with the aqueous extract of *Ocimum basilicum* to form a biosynthesized silver nanoparticle mixture. The average particle size and shape of the composition are determined by an array of factors that include, without limitation, the pH of the reaction mixture, the duration and the temperature of the reducing, the concentration of the silver salt and the concentration of the aqueous extract of *Ocimum basilicum* in the reaction mixture, the parts of *Ocimum basilicum* used to make the aqueous extract of *Ocimum basilicum*, and the type of *Ocimum basilicum* used. With respect to the type of *Ocimum basilicum* that may be used to make the aqueous extract, there are thousands of *Ocimum basilicum* available which are classified based on plant morphology, pigmentation, and chemical composition of the essential oils.

The effects of the above mentioned factors on the average particle size and shape of the composition may be unpredictable for the following reasons.

The composition includes the biosynthesized silver nanoparticles covered with, adsorbed with, attached to, and/or bonded with the components (e.g. phytochemicals and/or metabolites) from the aqueous extract of *Ocimum basilicum*. Some of the phytochemicals and/or metabolites are believed to stabilize the biosynthesized silver nanoparticles, e.g. capping proteins, which provide surface charge to the biosynthesized silver nanoparticles to control their agglomeration. The carbonyl groups from the amino acid residues of capping proteins have a strong ability to bind metal including silver. In one embodiment, the capping proteins may form a multi-layered protein shell covering the biosynthesized silver nanoparticles (See Navin Jain, Arpit Bhargava, Mohit Rathi, R. Venkataramana Dilip, Jitendra Panwar, Removal of Protein Capping Enhances the Antibacterial Efficiency of Biosynthesized Silver Nanoparticles, Plos One Jul. 30, 2015, incorporated herein by reference in its entirety). The identity of the capping proteins in the aqueous extract of *Ocimum basilicum* is poorly understood. One of the capping proteins may be keratin, which has been shown to have the ability to stabilize silver nanoparticles (See Peter Irwin, Justin Martin, Ly-Huong Nguyen, Yiping He, Andrew Gehring, Chin-Yi Chen, Antimicrobial activity of spherical silver nanoparticles prepared using a biocompatible macromolecular capping agent: evidence for induction of a greatly prolonged bacterial lag phase, Journal of Nanobiotechnology 2010, 8:34, incorporated herein by reference in its entirety). Some of the phytochemicals and/or metabolites are believed to be involved in both the reduction of the silver salt and stabilization of the biosynthesized silver nanoparticles. Although it is believed that phytochemicals and/or metabolites involved in the reduction of the silver salt may include alkaloids, saponins, terpenoids, phenols, tannins, anthraquinones, anthocyanins, and amino acids with such functional groups as a carboxyl group, a carbonyl group, an amine group, a hydroxyl group, and an alkene group, the precise identity of the reducing and/or stabilizing phytochemicals and/or metabolites remain poorly defined. Additionally, the abundance and activity of the reducing and/or stabilizing phytochemicals and/or metabolites may vary among different plants, among different types of *Ocimum basilicum*, and among different parts of the same plant. Further, the reducing and/or stabilizing activity of the unknown phytochemicals and/or metabolites likely vary under different biosynthesis conditions, such as the reaction pH, reaction temperature, and reaction duration, and the silver salt concentration and plant extract concentration in the reaction mixture, in a linear, or more likely, a non-linear fashion. For example, under the biosynthesis conditions in one embodiment of the present disclosure, reacting a silver nitrate solution with an aqueous leaf extract of *Ocimum basilicum* results in the formation of the composition comprising spherical biosynthesized silver nanoparticles with an average particle diameter of 30-50 nm. Under a set of different biosynthesis conditions, reacting a silver nitrate solution with an aqueous leaf extract of *Ocimum basilicum* of probably a different origin or type resulted in the formation of spherical biosynthesized silver nanoparticles with an average particle diameter of 88-120 nm (See E. Jayapriya and P. Lalitha, Synthesis of Silver Nanoparticles using Leaf Aqueous Extract of *Ocimum basilicum* (L.), International Journal of ChemTech Research, Vol. 5, No. 6, pp 2985-2992, October-December 2013, incorporated herein by reference in its entirety). As still another example, reacting a silver salt with a stem extract and a root extract of *Ocimum* sanctum under yet another set of biosynthesis conditions resulted in the formation of biosynthesized silver nanoparticles of 5±1.5 nm and 10±2 nm in average particle size, respectively (See Naheed Ahmad, Seema Sharma, Md. K. Alam, V. N. Singh, S. F. Shamsi, B. R. Mehta, Anjum Fatma, Rapid synthesis of silver nanoparticles using dried medicinal plant of basil, Colloids and Surfaces B: Biointerfaces, Volume 81, Issue 1, 1 Nov. 2010, Pages 81-86, incorporated herein by reference in its entirety).

In some embodiments, the composition is of uniform shape, i.e. at least 75%, preferably at least 80%, more preferably at least 90%, or more preferably at least 95%, of the composition is of one shape, non-limiting examples of which include a spherical shape, a triangular shape, a rod shape, or a cubic shape.

In other embodiments, the composition may have different shapes, for example, any combinations of a spherical shape, a triangular shape, a rod shape, or a cubic shape, with the composition of each shape being present at 25-75% of the total population of the composition.

In some embodiments, the composition has an average particle size of 5-80 nm, 10-70 nm, preferably 20-60 nm, or more preferably 30-50 nm. The average particle size of the composition is an average particle diameter when the composition has a spherical shape. The average particle size of the composition is an average of the longest particle edge length when the composition has a triangular shape. The average particle size of the composition is an average of the particle length when the composition has a rod shape. The average particle size of the composition is an average length of the cubic particle edge when the composition has a cubic shape.

To detect $Hg^{2+}$ in an aqueous solution, in one embodiment, the contacting of the composition comprising a plant extract and biosynthesized silver nanoparticles with the aqueous solution is done by adding an appropriate amount of the composition suspended in water, preferably deionized water, preferably distilled water, or more preferably double distilled water, to the aqueous solution, optionally and preferably followed by gentle mixing, for example, by gently tapping the container or tube containing the resulting mixture or by vortexing the resulting mixture at a low speed. In another embodiment, an appropriate amount of the composition suspended in water may be first centrifuged, for example, at a speed of 10,000-17,000 rpm for 5-30 minutes, or for 10-20 minutes, to pellet the composition. Then, immediately after removing the supernatant, the composition may be re-suspended in the aqueous solution containing $Hg^{2+}$. This embodiment is preferred when the detection requires a large amount of the composition and a dilution of the aqueous solution containing $Hg^{2+}$ by an addition of a large volume of the composition/water suspension is not desirable. It is within the ability of a person of ordinary skill in the art to determine the appropriate amount of the composition needed to detect $Hg^{2+}$ in an aqueous solution. For example, the appropriate amount may be determined by using a series of $Hg^{2+}$ containing aqueous solutions of known concentrations, with the known concentrations establishing a concentration range that preferably encompasses the unknown $Hg^{2+}$ concentration of the $Hg^{2+}$ containing aqueous solution to be detected, as positive control samples.

The mixture of the composition and the $Hg^{2+}$ containing aqueous solution undergoes a color change from a golden brown or a yellowish brown color to pale yellow or to colorless with increasing $Hg^{2+}$ concentrations in the mixture.

In one embodiment, at a certain concentration range of $Hg^{2+}$, e.g. a $Hg^{2+}$ concentration of greater than 0.1 mM, or greater than 0.5 mM, or greater than 1 mM, the color change of the mixture can be detected by the naked eye. In another embodiment, the color change of the mixture can be detected and quantified by UV-visible spectrophotometry, particularly when the $Hg^{2+}$ concentration is low, e.g. when the $Hg^{2+}$ concentration is lower than 0.1 mM, or lower than 0.05 mM, or lower than 0.01 mM, or lower than 0.005 mM, or lower than 0.001 mM. When the color change of the mixture is detected and quantified by UV-visible spectrophotometry, the composition and the $Hg^{2+}$ are preferably allowed to interact sufficiently, for example, by allowing the composition to interact with the $Hg^{2+}$ for at least 3 minutes, preferably at least 5 minutes, or preferably at least 10 minutes, before the absorbance of the mixture is measured, preferably at a wavelength of about 360-500 nm, about 370-480 nm, about 380-450 nm, about 390-430 nm, about 395-410 nm, about 390-410 nm, or more preferably at about 400 nm. The color change is quantified as the difference between the absorbance of the mixture and the absorbance of a blank control which is a mixture of the same amount of the composition and water of the same volume as the volume of the $Hg^{2+}$ containing aqueous solution. In some embodiments, the difference between the absorbance of the mixture and the absorbance of the blank control is at least 0.5%, at least 0.8%, at least 1%, at least 1.5%, at least 2%, at least 2.5%, at least 3%, at least 4%, or at least 5%, of the absorbance of the blank control to indicate a color change by the UV-visible spectrophotometry. In some embodiments, the detection by UV-visible spectrophotometry is performed by measuring the absorbance of the mixture and the blank control at a single wavelength within a range described above. In other embodiments, the detection by UV-visible spectrophotometry is preferably performed by measuring the absorbance of the mixture and the blank control at a plurality of wavelengths covering an entire wavelength range described above and selecting the absorbance values at a wavelength where the blank control has the highest absorbance to calculate the difference in absorbance between the mixture and the blank control. In other embodiments, the detection by UV-visible spectrophotometry is performed in an automated and/or high throughput fashion, e.g. using a plate reader, either at a single wavelength or at a plurality of wavelengths covering an entire wavelength range.

In some embodiments, the magnitude of the color change detected by the UV-visible spectrophotometry linearly correlates with the concentration of $Hg^{2+}$ in the aqueous solution ranging from about 0.1 µM to 300 µM, from about 0.3 µM to 250 µM, from about 0.5 µM to about 200 µM, from about 0.7 µM to about 150 µM, from about 1 µM to about 90 from about 1.5 µM to about 70 µM, from about 2 µM to 50 µM, or from about 5 µM to 30 µM.

In some embodiments, the lowest concentration of $Hg^{2+}$ in the aqueous solution detected by the UV-visible spectrophotometry is about 10-500 nM, about 20-400 nM, 30-300 nM, about 40-200 nM, about 50-100 nM, or about 60-80 nM.

Farhadi K. et al reported a $Hg^{2+}$ detection limit of $2.2 \times 10^{-6}$ M (i.e. 2.2 µM) using biosynthesized silver nanoparticles prepared by reacting a silver nitrate aqueous solution with an aqueous extract of manna of hedysarum plant as a reducing agent (See Khalil Farhadi, Mehrdad Forough, Rahim Molaei, Salahaddin Hajizadeh, Aysan Rafipour, Highly selective $Hg^{2+}$ colorimetric sensor using green synthesized and unmodified silver nanoparticles, Sensors and Actuators B: Chemical, Volume 161, Issue 1, 3 Jan. 2012, Pages 880-885, incorporated herein by reference in its entirety). The much lower $Hg^{2+}$ detection limit in the nM range obtainable by the disclosed method is unexpected, since the $Hg^{2+}$ detection limit is believed to be affected at least by the average particle size of the biosynthesized silver nanoparticles and the distance between the biosynthesized silver nanoparticles dictated by the extent of agglomeration of the biosynthesized silver nanoparticles. As described above, the average particle size of the biosynthesized silver nanoparticles prepared with an *Ocimum* plant extract has a wide range of 5-120 nm under different biosynthesis conditions. There are a large number of different permutations of the biosynthesis conditions, and the average particle size of the biosynthesized silver nanoparticles obtainable under a specific set of biosynthesis conditions is unpredictable. Additionally, although silver nanoparticles of a smaller average particle size are believed to have a higher detection sensitivity for $Hg^{2+}$, or a lower $Hg^{2+}$ detection limit, because of their larger aggregate surface area, smaller silver nanoparticles have a stronger tendency to agglomerate that decreases the net gain in surface area. Further, an increased concentration of silver nanoparticles formed during biosynthesis may also promote agglomeration. Thus, the average particle size range of the biosynthesized silver nanoparticles leading to an advantageous $Hg^{2+}$ detection limit is difficult to predict and/or attain due to the opposing effects of a larger aggregate surface area and a stronger tendency to agglomerate associated with smaller silver nanoparticles and/or due to the selection of the *Ocimum* species and specific biosynthesis conditions. The advantageous $Hg^{2+}$ detection limit disclosed herein is believed to result from an unexpectedly good balance between a relatively small average particle size of the composition comprising the biosynthesized silver nanoparticles and a relatively moderate agglomeration of the biosynthesized silver nanoparticles.

The disclosed $Hg^{2+}$ detection method is highly selective and specific for detecting $Hg^{2+}$ in an aqueous solution in a colorimetric fashion without interference from other transition metal ions, e.g. $Ni^{2+}$, $Mn^{2+}$, $Cu^{2+}$, $Zn^{2+}$, $Co^{2+}$, and $Cd^{2+}$, from alkali metal ions, e.g. $Li^+$, $Na^+$, and $K^+$, and from alkaline earth metal ions, e.g. $Mg^{2+}$, $Ca^{2+}$, $Sr^{2+}$, and $Ba^{2+}$. More specifically, when the composition contacts $Hg^{2+}$ in an aqueous solution, the resulting mixture changes color from golden or yellowish brown to pale yellow or to colorless. By contrast, when the composition contacts an aqueous solution containing any of the above non-$Hg^{2+}$ metal ions or their combinations, there is no or negligible color change of the composition-aqueous solution mixture. In some embodiments, the above non-$Hg^{2+}$ metal ions can be present at a concentration of 0-5 mM, preferably 0-3 mM, preferably 0-1 mM, more preferably 0-0.8 mM, more preferably 0-0.5 mM, or more preferably 0-0.3 mM, or more preferably 0-0.1 mM, in the aqueous solution without interfering with the $Hg^{2+}$ detection and quantification. The disclosed $Hg^{2+}$ detection method can be performed at a temperature of about 4-100° C., preferably about 10-80° C., preferably about 20-60° C., or preferably about 25-50° C.

The disclosed $Hg^{2+}$ detection method may be performed at a pressure of about 0.1-100 bar, about 0.5-80 bar, preferably about 1-50 bar, preferably about 1-30 bar, preferably about 1-20 bar, or preferably about 1-10 bar.

It is well known that different types of mercury, including elemental Hg, $Hg(OH)_2$, HgO, $CH_3Hg^+$ and $CH_3HgCl$ can be transformed into water-soluble $Hg^{2+}$ ions by using a digestive method well known in the art. For example, a mercury-containing sample, such as a biological tissue, a lake sediment, and a soil sample, may be digested using 5-7:3-5 $HNO_3$:$H_2SO_4$ (vol:vol) and heat. Bromine monochloride (BrCl) is then added to the sample to oxidize all forms of Hg to Hg (II) oxidation state. Thus, in some embodiments, the disclosed $Hg^{2+}$ detection method may be used for detecting and quantifying total mercury content derived from all the above mentioned mercury forms.

Having generally described this invention, a further understanding can be obtained by reference to certain specific examples which are provided herein for purposes of illustration only and are not intended to be limiting unless otherwise specified.

For simplicity of description, the "composition" comprising a plant extract and biosynthesized silver nanoparticles described above is called "biosynthesized silver nanoparticles," "biosynthesized silver nanoparticle," "biosynthesized AgNPs," or "biosynthesized AgNP" in the following examples.

EXAMPLE 1

Materials and Methods 1.1. Instruments

UV-visible spectrophotometry analyses were carried out using a single beam, Specord 50 UV-visible spectrophotometer (Analytik Jena) with a 1.0 cm quartz cell. Surface morphology characterization was carried out using field emission scanning electron microscopy (Lyra3 TESCAN FESEM). This FESEM was also equipped with an energy-dispersive X-ray spectroscope (EDS) detector. Fourier transform infrared spectroscopy analysis of the sample was done using a Nicolet 6700 FT-IR (Thermo Electron Corporation). X-ray diffractometry (XRD) analysis was done using Rigaku Miniflex II desktop X-ray diffractometer with a tube output voltage of 30 kV.

1.2. Chemicals and Materials

The chemicals used were of analytical grade and used with no further purification. Silver nitrate was purchased from Merck, Germany. The salts used included NaCl, $CaCl_2$, $BaCl_2.2H_2O$, $Zn(NO_3)_2.6H_2O$, $NiCl_2.6H_2O$, $MnSO_4.H_2O$, $HgCl_2$, $CuSO_4.5H_2O$ and KCl, all of which were purchased from Merck or Fischer chemical companies and used without further purification. All solutions were prepared using Milli-Q water. 0.1 M solutions of hydrochloric acid and sodium hydroxide were used in adjusting pH when necessary. All glassware was cleaned with diluted nitric acid and rinsed in Milli-Q water before use.

1.3. Biosynthesis of Silver Nanoparticles (AgNPs)

Figure 2:
FIG. 2 a picture showing *Ocimum basilicum* with the leaves according to Example 1.

A basil (*Ocimum basilicum*) plant, shown in FIGS. 1 and 2, was obtained from King Fand University of Petroleum and Minerals. 20 g of the leaves and 20 g of the flowers of the plant were boiled in 300 mL of deionized water to obtain a plant broth or extract. The plant broth or extract was then filtered and stored in a refrigerator at 4° C. until further use. Silver nitrate solutions of different silver nitrate concentrations were mixed with varying volumes of the plant extract according to pre-determined volume ratios of the plant extract to the silver nitrate solution to form reaction mixtures where silver nitrate reacted with the plant extract to form corresponding biosynthesized silver nanoparticle mixtures via reduction of $Ag^+$ by phytochemicals and/or metabolites present in the plant extract. The plant extract was added to the silver nitrate solution drop-wise and a change in the color of the reaction mixture was observed. The reduction of silver nitrate by the plant extract to form the biosynthesized AgNPs was monitored using UV-visible spectrophotometry.

1.4. Determination of the Effects of Various Factors on the Biosynthesis of Silver Nanoparticles The effects of various factors, such as the pH of the reaction mixture, the temperature and duration of the reaction, and the plant extract concentration and silver nitrate concentration in the reaction mixture on the formation of the biosynthesized silver nanoparticles (AgNPs) were studied. To determine the effect of pH on the biosynthesis of AgNPs, the biosynthesis reaction was carried out at different pH conditions of 4, 7, 8, and 10. The effect of temperature was determined by carrying out the biosynthesis reaction at 25° C., 40° C. and 70° C. The effect of reaction time was determined by allowing the reaction to last for 15, 30, 60, 90, 120, 240 and 480 min. To study the effect of the plant extract concentration in the reaction mixture, the plant extract was mixed with a 1 mM silver nitrate solution with the volume ratios of the plant extract to the 1 mM silver nitrate solution set at 1:1, 1:10, 1:20, 1:25, 1:50, 1:100 and 1:200. The effect of the silver nitrate concentration in the reaction mixture was investigated by varying the silver nitrate concentration of the silver nitrate solution, which was 1 mM, 2 mM, or 5 mM.

1.5. Characterization of the Biosynthesized AgNPs

The biosynthesized AgNPs were characterized using different techniques. The reduction of $AgNO_3$ by the plant extract was confirmed using a Specord 50 single beam UV spectrophotometer scanning from 300 nm to 800 nm in wavelength at a 1-nm resolution. The UV-visible spectrophotometry analysis was carried out with a 10-fold diluted biosynthesized silver nanoparticle mixture. The shape and average particle size of the biosynthesized silver nanoparticles were analyzed by using scanning electron microscopy. The elemental composition of the biosynthesized silver nanoparticles was determined by using elemental dispersive X-ray spectroscopy. The biosynthesized AgNPs were characterized using Fourier Transform Infrared Spectrophotometer (FTIR) to determine the phytochemicals that took part in the reduction of $AgNO_3$ to biosynthesized AgNPs and in the subsequent capping of the biosynthesized silver nanoparticles to form a coating on the biosynthesized silver nanoparticles to keep the biosynthesized silver nanoparticles stable. X-ray diffractometry (XRD) was used to determine the phase purity and the crystal phase identification of the biosynthesized silver nanoparticles.

1.6. Colorimetric Detection of $Hg^{2+}$ in an Aqueous Solution

To detect $Hg^{2+}$ in an aqueous solution using the biosynthesized AgNPs, 1 mL of the biosynthesized AgNPs was added to 9 mL of deionized water to make a 10-fold diluted biosynthesized AgNP mixture as a blank control. To determine the detection limit of $Hg^{2+}$ with the biosynthesized silver nanoparticles, triplicate samples were prepared by adding 1 mL of the biosynthesized AgNPs to 9 mL of each one of a series of $Hg^{2+}$ containing aqueous solutions with different $Hg^{2+}$ concentrations. Additionally, to examine the selectivity of the biosynthesized AgNPs for the colorimetric detection of $Hg^{2+}$, 1 ml of the biosynthesized AgNPs was added to 9 mL of an aqueous solution containing 1 mM of each of the following metal ions: $Ca^{2+}$, $Cu^{2+}$, $Mn^{2+}$, $Ni^{2+}$, $Na^+$, $Zn^{2+}$, $Ba^{2+}$, and $K^+$. The analysis was carried out using UV-visible spectrophotometry.

EXAMPLE 2

Biosynthesis of the Silver Nanoparticles with the Plant Extract from *Ocimum basilicum*

Figure 3:
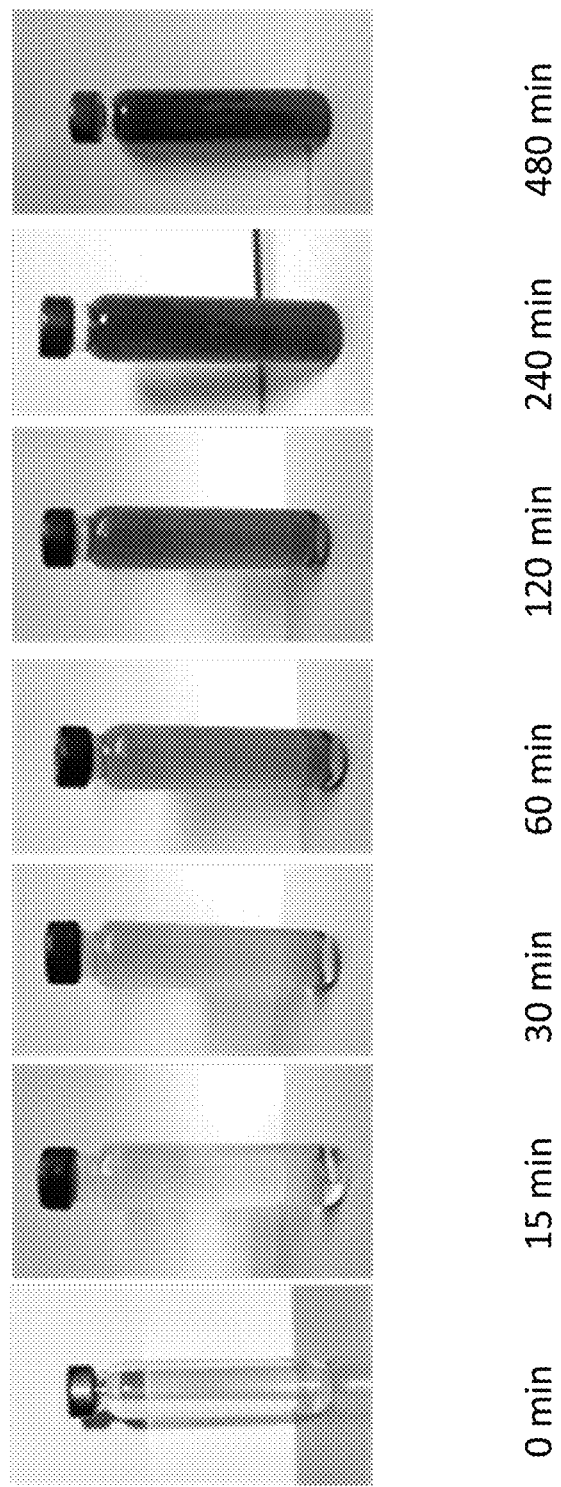
FIG. 3 is a picture showing the reaction mixtures of a silver nitrate solution and an extract of *Ocimum basilicum* at various reaction time points of 0, 15, 30, 60, 120, 240 and 480 minutes according to Example 2.

After adding the plant extract drop-wise into the silver nitrate solution, the resulting reaction mixture was clearer, or more transparent and colorless than the silver nitrate solution, indicating the start of the reaction. The color change of the reaction mixture with time is shown in FIG. 3. The steady darkening of the reaction mixture from brown to golden brown indicated a continuous reduction of silver nitrate to biosynthesized AgNPs and an increase in the concentration or formation of biosynthesized AgNPs in the reaction mixture. The formation of biosynthesized AgNPs was characterized by the excitation of surface plasmon resonance vibrations in biosynthesized silver nanoparticles that resulted in a color change.

EXAMPLE 3

Effect of Various Factors on the Biosynthesis of Silver Nanoparticles

Figure 4:
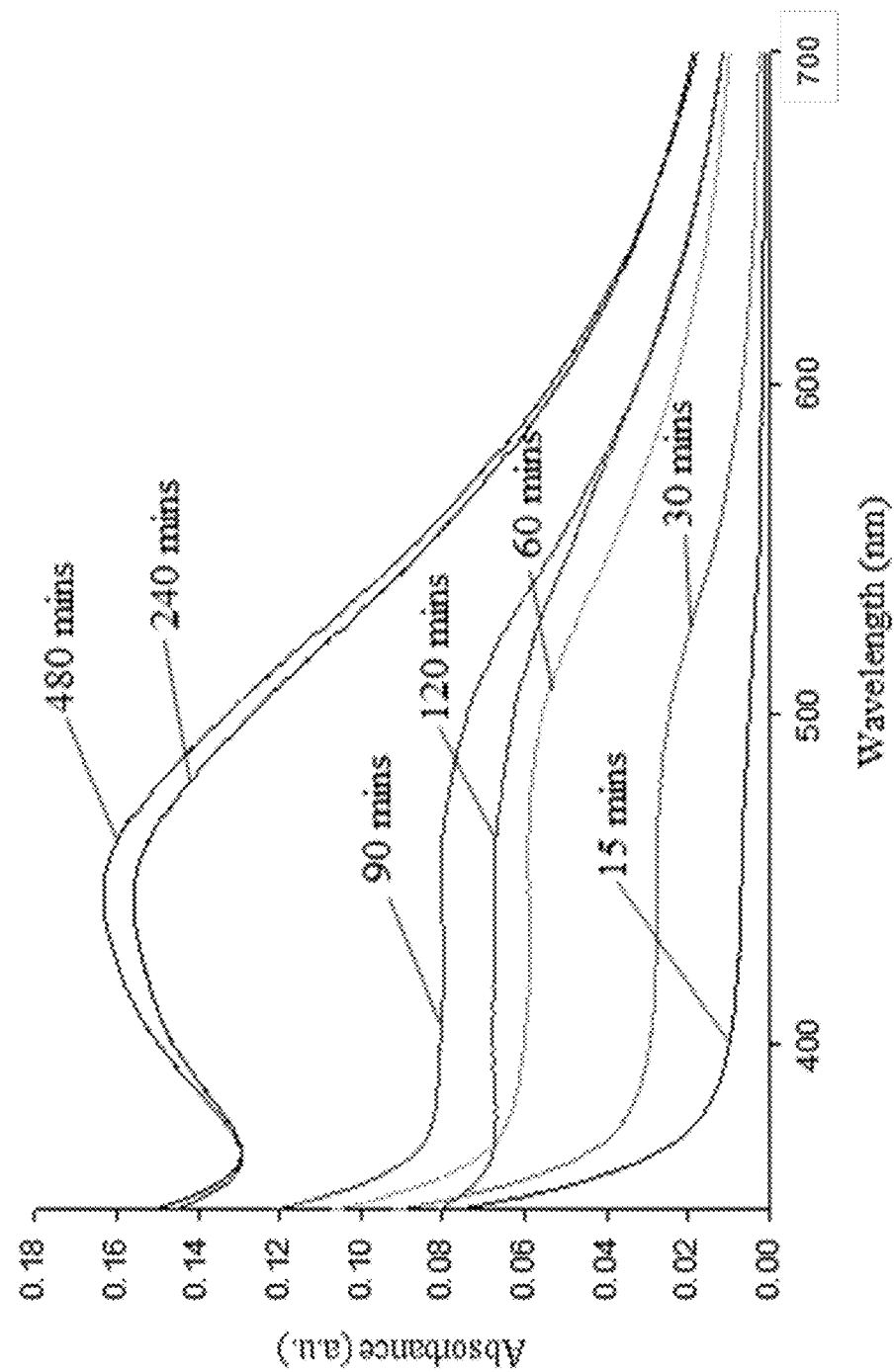
FIG. 4 is a graphical presentation of the UV-visible spectra showing the effect of reaction time on the biosynthesis of silver nanoparticles at neutral pH and room temperature according to Example 3.

Referring the FIG. 4 depicting the absorbance versus the wavelength from the UV-visible spectrophotometry analysis for the effect of reaction time on the biosynthesis of AgNPs after mixing the silver nitrate solution with the plant extract at neutral pH and room temperature. No strong peak was observed within the first 120 mins after the commencement of the reaction. A pronounced peak became visible at 240 mins, which further increased from 240 mins to 480 mins. The gradual formation of the peak may be attributed to an increase in the biosynthesized silver nanoparticles formed in the reaction mixture and exhibiting light-excited surface plasmon resonance vibrations. The difference between the peak formed at time 240 mins and the peak formed at time 480 mins, however, was insignificant, indicating that the reduction of silver nitrate had almost reached completion at 240 min. Having shifted from a weak peak at above 450 nm in wavelength formed at an earlier time, e.g. at 90 min and 120 min, the peaks formed at time 240 min and 480 mM were within the wavelength range of 430-440 nm, indicating a gradual reduction in the average particle size of the biosynthesized AgNPs formed during the 240-480 min time frame.

Figure 5:
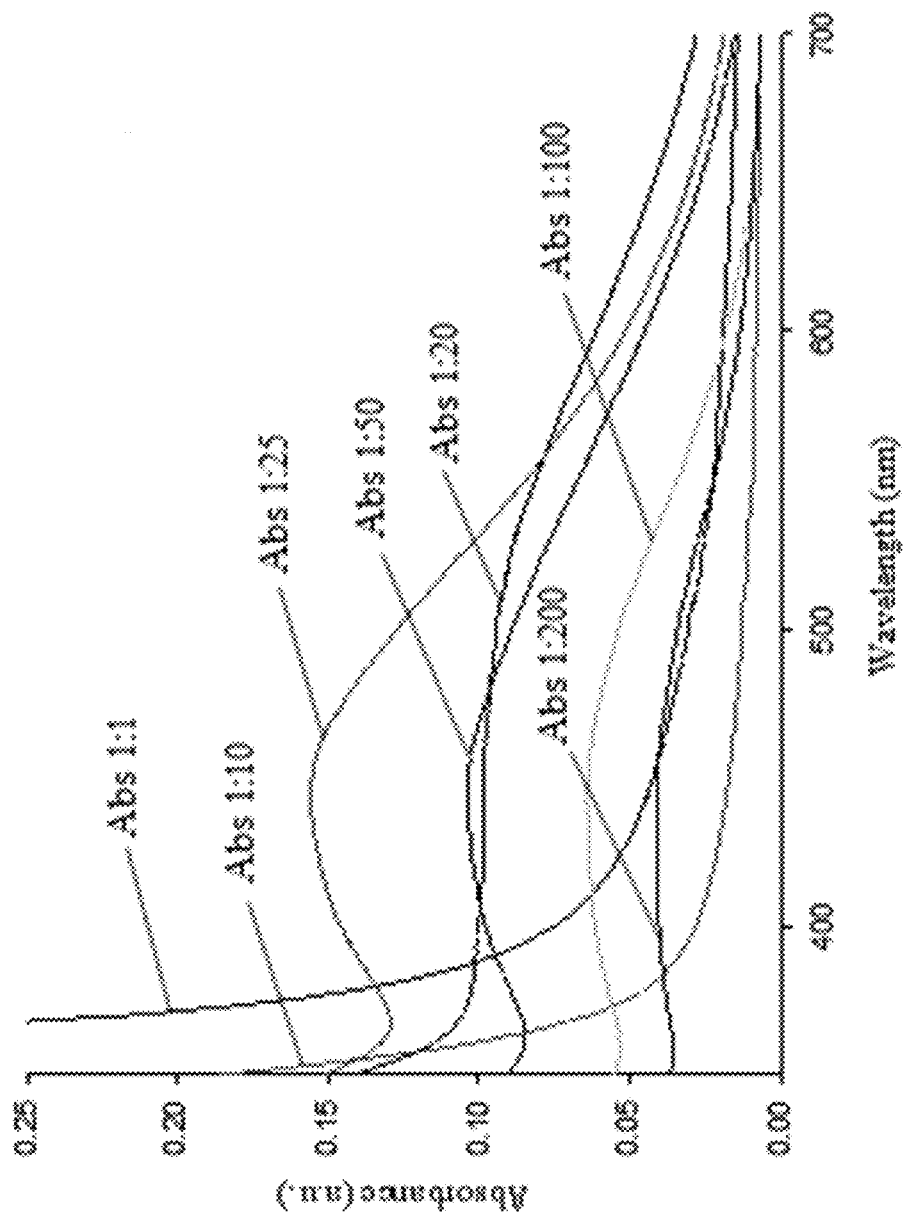
FIG. 5 is a graphical presentation of the UV-visible spectra showing the effect of the volume ratio of the extract of *Ocimum basilicum* to the silver nitrate solution on the biosynthesis of silver nanoparticles according to Example 3.

Referring to FIG. 5 depicting the absorbance versus the wavelength from the UV-visible spectrophotometry analysis for the effect of the plant extract concentration in the reaction mixture on the biosynthesized AgNP formation. The plant extract was mixed with a silver nitrate solution at different volume ratios as indicated. The highest peak in absorbance was observed at the volume ratio of 1:25, indicating that that all the silver ions had reacted with the plant extract at this volume ratio. Thus, 1:25 was a preferred volume ratio of the plant extract to the silver nitrate solution under which a complete reaction (reduction) of $AgNO_3$ with the plant extract took place to obtain the maximum formation of the biosynthesized silver nanoparticles.

Figure 6:
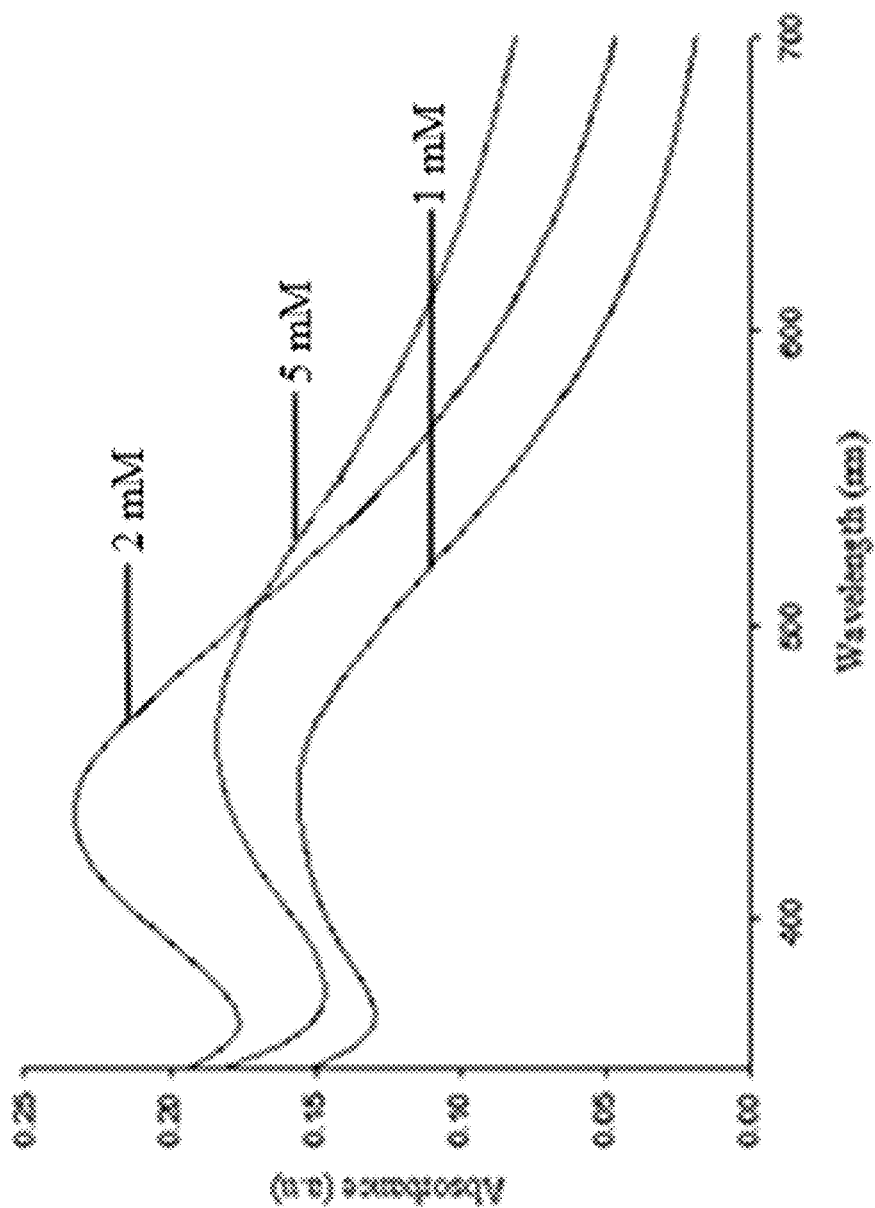
FIG. 6 is a graphical presentation of the UV-visible spectra showing the effect of the silver nitrate concentration in the silver nitrate solution on the biosynthesis of silver nanoparticles according to Example 3.

Referring to FIG. 6 depicting the absorbance versus the wavelength from the UV-visible spectrophotometry analysis for the effect of the silver nitrate concentration in the silver nitrate solution (and consequently the silver nitrate concentration in the reaction mixture) on the biosynthesized AgNP formation, with the duration and temperature of the reaction, the pH of the reaction mixture, and the plant extract concentration in the reaction mixture kept constant. As the silver nitrate concentration in the silver nitrate solution was reduced from 5 mM to 1 mM, the wavelength of the peak absorbance was shifted closer to 400 nm. The largest peak absorbance was obtained when the silver nitrate concentration in the silver nitrate solution was 2 mM, indicating that the reduction of silver nitrate by the plant extract was the most complete at this silver nitrate concentration as compared to the other two silver nitrate concentrations of 1 mM and 5 mM.

Figure 7:
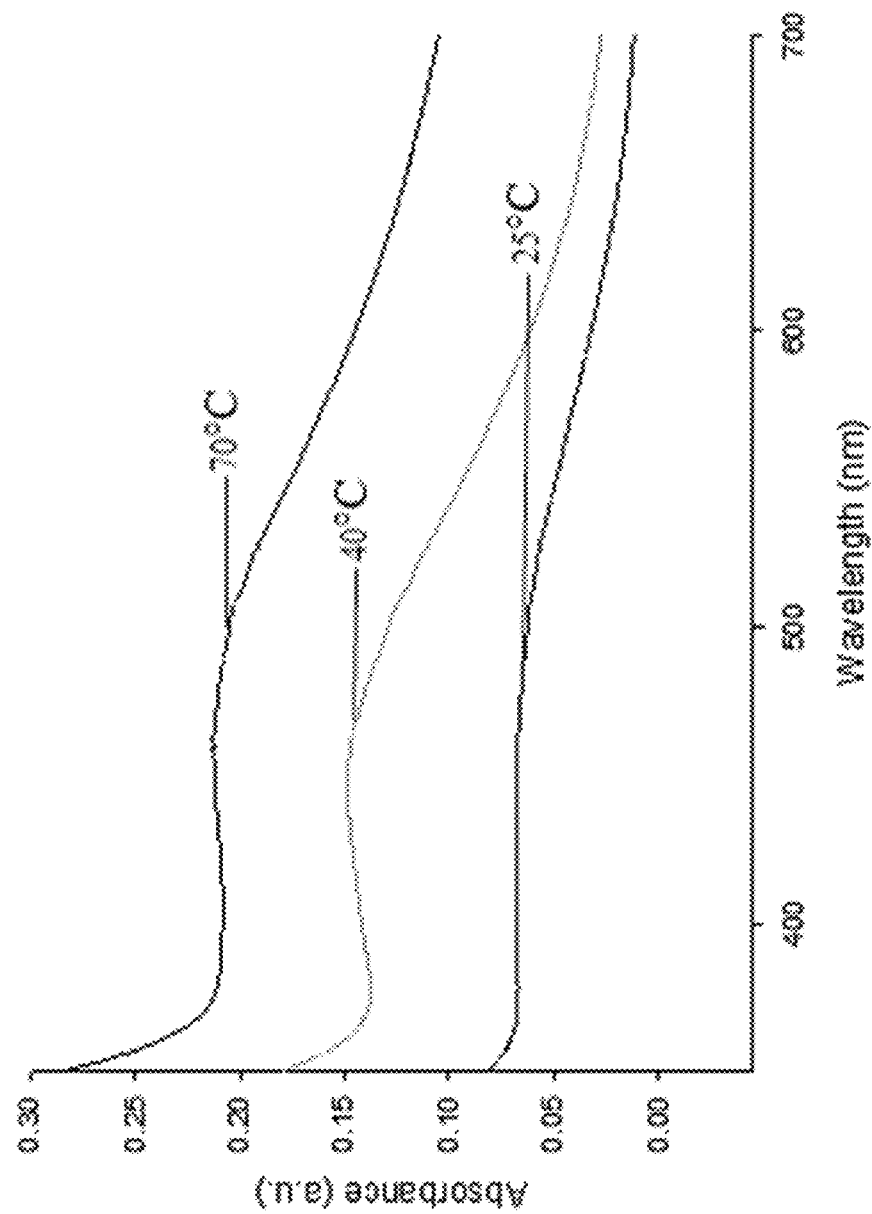
FIG. 7 is a graphical presentation of the UV-visible spectra showing the effect of temperature on the biosynthesis of silver nanoparticles according to Example 3.

Referring to FIG. 7 depicting the absorbance versus the wavelength from the UV-visible spectrophotometry analysis for the effect of the reaction temperature on the biosynthesized silver nanoparticle formation with the reaction time fixed at 1 h. Although the absorbance peak formed at each temperature was not particularly pronounced, the value of the absorbance at 70° C. was the highest, indicating that the formation of the biosynthesized silver nanoparticles increased with the increasing reaction temperature.

Figure 8:
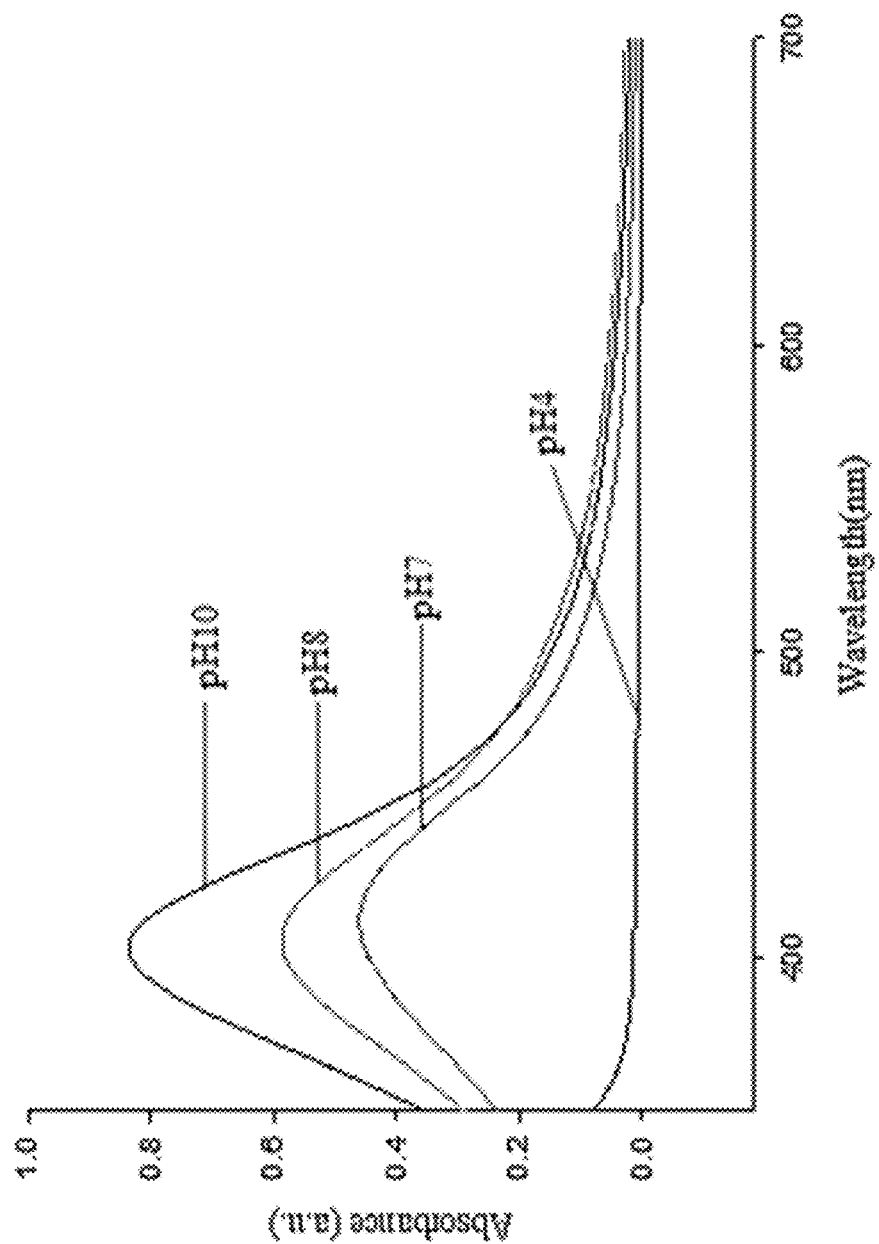
FIG. 8 is a graphical presentation of the UV-visible spectra showing the effect of pH of the reaction mixture comprising the silver nitrate solution and the extract of *Ocimum basilicum* on the biosynthesis of silver nanoparticles according to Example 3.

Referring to FIG. 8 depicting the absorbance versus the wavelength from the UV-visible spectrophotometry analysis for the effect of pH on the formation of biosynthesized AgNPs. The absorbance peaks occurring at pH 7 and particularly at pH 8 and pH 10 were larger and at a wavelength closer to 400 nm as compared to the absorbance peaks in the spectra obtained from the studies examining the effects of other factors described above, in which the pH of the reaction mixture was acidic and not raised by the addition of NaOH, indicating that the formation of biosynthesized AgNPs, particularly of smaller average particle size, e.g. about 30 nm and/or less than 30 nm, was favored as the reaction mixture became increasingly basic and consistent with the 2013 finding by Vanaja that the excitation of the surface plasmon resonance of silver nanoparticles was supported in an alkaline medium (See Vanaja, M., Gnanajobitha, G., Paulkumar, K., Rajeshkumar, S., Malarkodi, C., & Annadurai, G. (2013). Phytosynthesis of silver nanoparticles by Cissus quadrangularis: influence of physicochemical factors. *Journal of Nanostructure in Chemistry*, 3(1), 17, incorporated herein by reference in its entirety).

Additionally, the peak absorbance increased with the increasing pH, with the highest peak absorbance obtained at pH 10 and at a wavelength of 402 nm, and with no distinct absorbance peak at pH 4, again indicating that the formation of biosynthesized AgNPs was supported in an alkaline medium but not in an acidic condition and consistent with the 2013 finding by Vanaja that the excitation of the surface plasmon resonance of silver nanoparticles was supported in an alkaline medium (See Vanaja, M., Gnanajobitha, G., Paulkumar, K., Rajeshkumar, S., Malarkodi, C., & Annadurai, G. (2013). Phytosynthesis of silver nanoparticles by Cissus quadrangularis: influence of physicochemical factors. *Journal of Nanostructure in Chemistry*, 3(1), 17, incorporated herein by reference in its entirety).

EXAMPLE 4

Characterization of the Biosynthesized Silver Nanoparticles

The biosynthesized silver nanoparticles were synthesized by reacting a 2 mM $AgNO_3$ solution with the plant extract for 2 hours at pH 10 and room temperature. The biosynthesized silver nanoparticles were then separated from the reaction mixture by centrifugation at 17,000 rpm, and were characterized by field emission scanning electron microscopy (FE-SEM) and FTIR.

Figure 9:
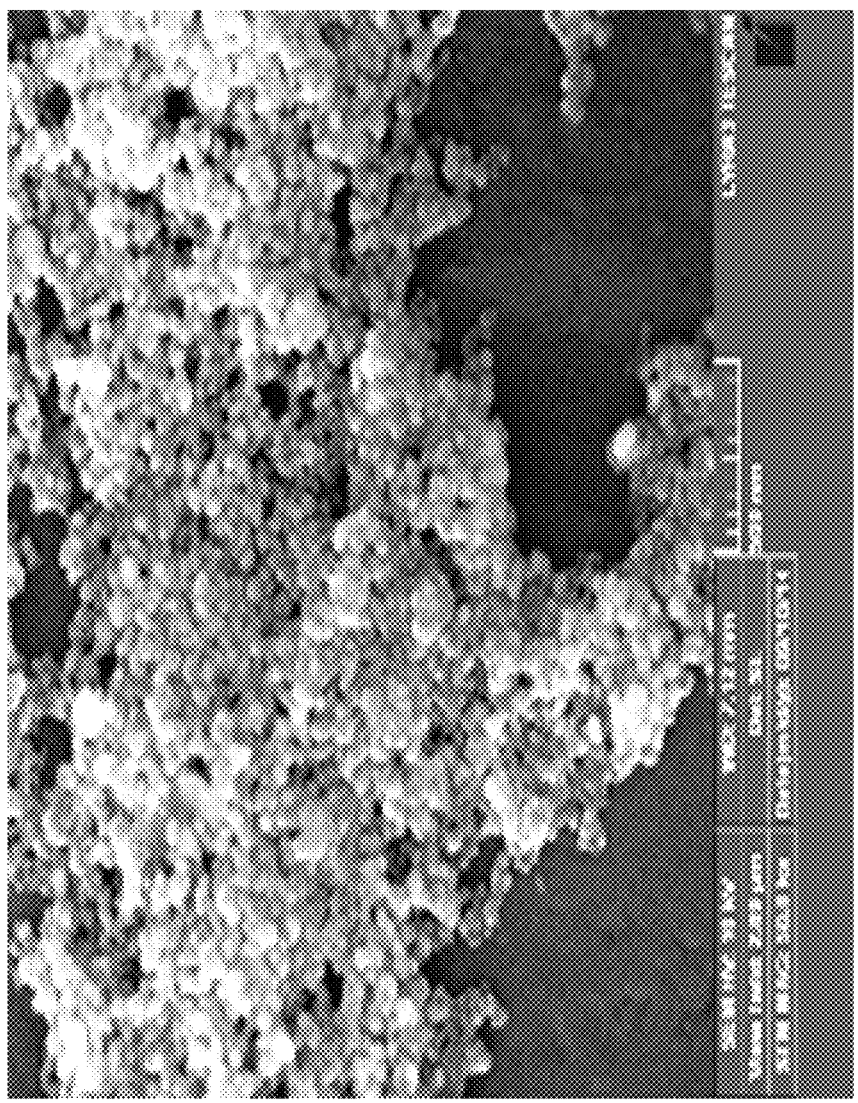
FIG. 9 is an FE-SEM image of the biosynthesized silver nanoparticles according to Example 4.
Figure 10:
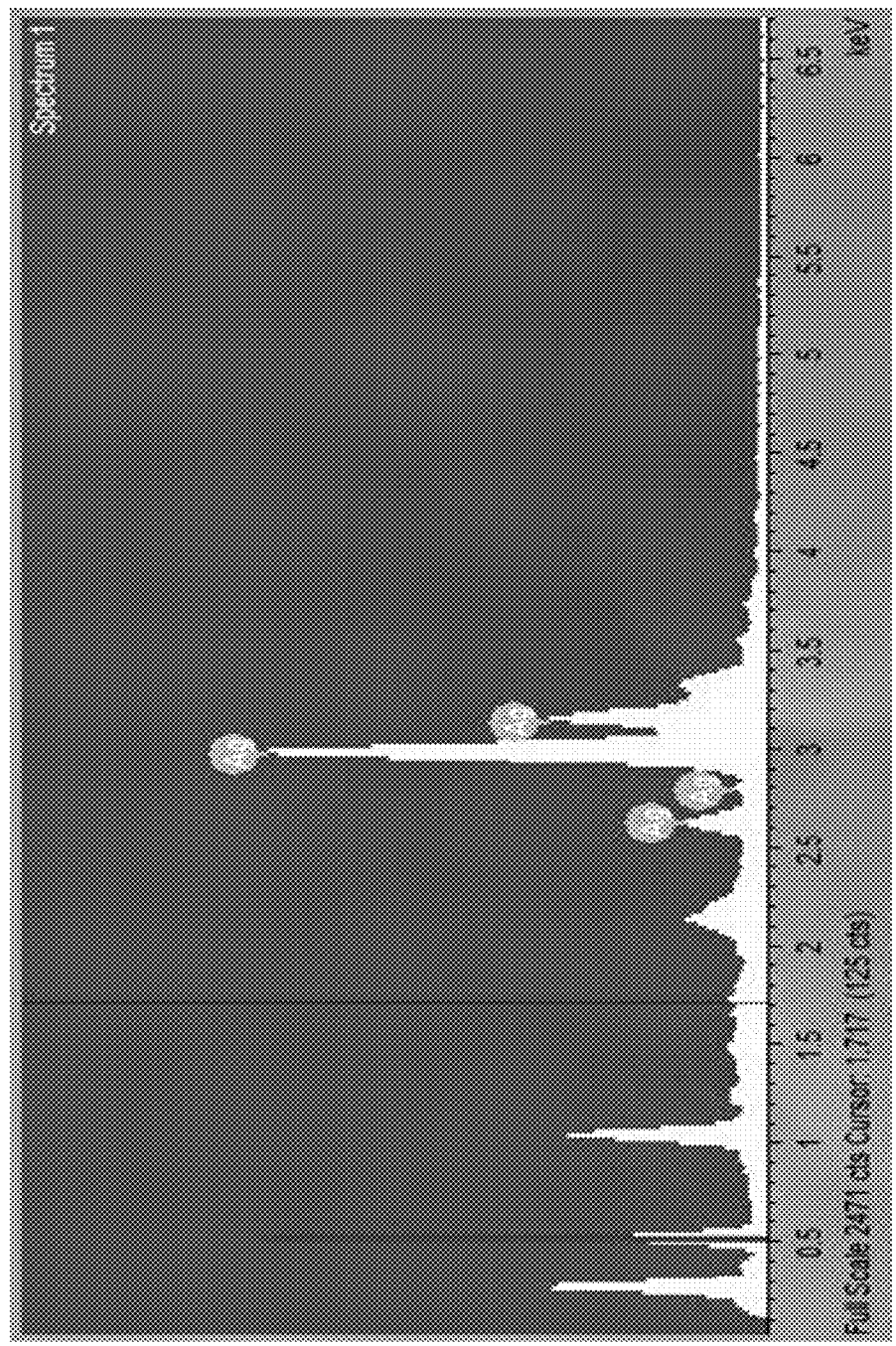
FIG. 10 is a graphical presentation of the EDS analysis data of the biosynthesized silver nanoparticles according to Example 4.

The SEM image in FIG. 9 shows the shape and morphology of the biosynthesized silver nanoparticles and provides an estimated average particle size of the biosynthesized silver nanoparticles. The image also shows agglomeration of the biosynthesized silver nanoparticles, which is believed to be controlled by the same phytochemicals and/or metabolites involved in the reduction of silver nitrate to biosynthesized silver nanoparticles and/or other substances from the plant extract. The biosynthesized silver nanoparticles were spherical and polydispersed, with an average particle size of 30-50 nm. The energy dispersive X-ray spectroscopy (EDS) data presented in FIG. 10 indicated that the biosynthesized silver nanoparticles mainly comprised silver.

Figure 11:
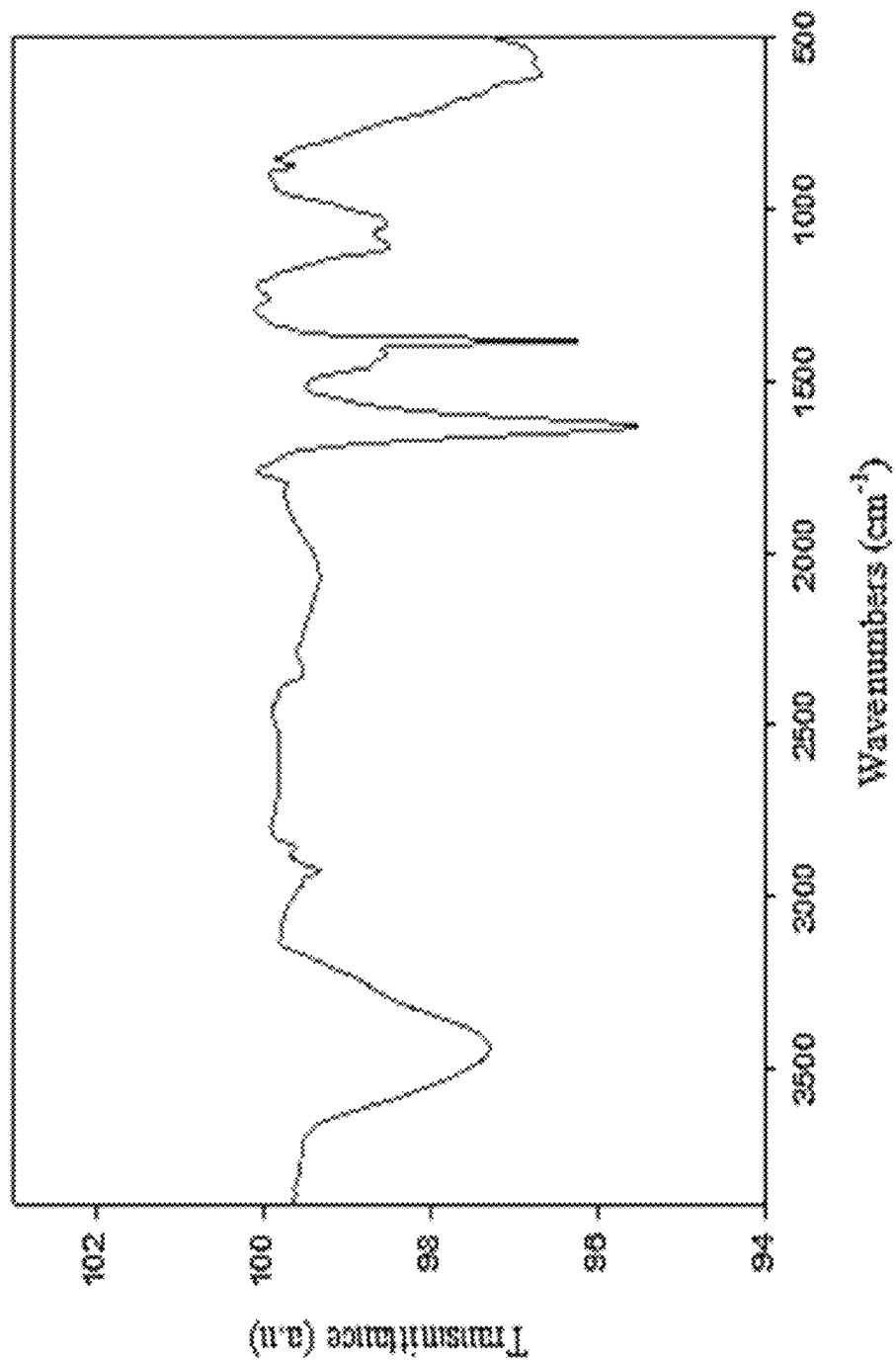
FIG. 11 is a graphical presentation of the FTIR spectra of the biosynthesized silver nanoparticles according to Example 4.

The result of the FTIR analysis shown in FIG. 11 revealed different absorption bands. The band seen at 3400 $cm^{-1}$ indicates either O—H stretching vibrations of hydroxyl groups (See Rastogi, L., & Arunachalam, J. (2011). Sunlight based irradiation strategy for rapid green synthesis of highly stable silver nanoparticles using aqueous garlic (*Allium sativum*) extract and their antibacterial potential. *Materials Chemistry and Physics*, 129(1-2), 558-563, incorporated herein by reference in its entirety) or N—H stretching of amine and amides (See Vanaja, M., Gnanajobitha, G., Paulkumar, K., Rajeshkumar, S., Malarkodi, C., & Annadurai, G. (2013). Phytosynthesis of silver nanoparticles by Cissus quadrangularis: influence of physicochemical factors. *Journal of Nanostructure in Chemistry*, 3(1), 17, incorporated herein by reference in its entirety). The band at 1600 $cm^{-1}$ indicates alkene stretching vibration (See Philip, D., & Unni, C. (2011). Extracellular biosynthesis of gold and silver nanoparticles using Krishna tulsi (*Ocimum sanctum*) leaf *Physica E: Low-Dimensional Systems and Nanostructures*, 43(7), 1318-1322, incorporated herein by reference in its entirety), while that at 1390 $cm^{-1}$ is assigned to O—H bending and indicates carboxylates (See Vanaja, M., Gnanajobitha, G., Paulkumar, K., Rajeshkumar, S., Malarkodi, C., & Annadurai, G. (2013). Phytosynthesis of silver nanoparticles by Cissus quadrangularis: influence of physicochemical factors. *Journal of Nanostructure in Chemistry*, 3(1), 17, incorporated herein by reference in its entirety). The band at 1080 $cm^{-1}$ indicates the absorption peak of —C—O—C—, while that at 600 $cm^{-1}$ indicates C—Cl stretching vibrations of alkyl halides. It can therefore be deduced that the functional groups of the phytochemicals and/or metabolites responsible for the reduction of the silver ions to the biosynthesized silver nanoparticles include carboxyl groups, amines and alkenes.

Figure 12:
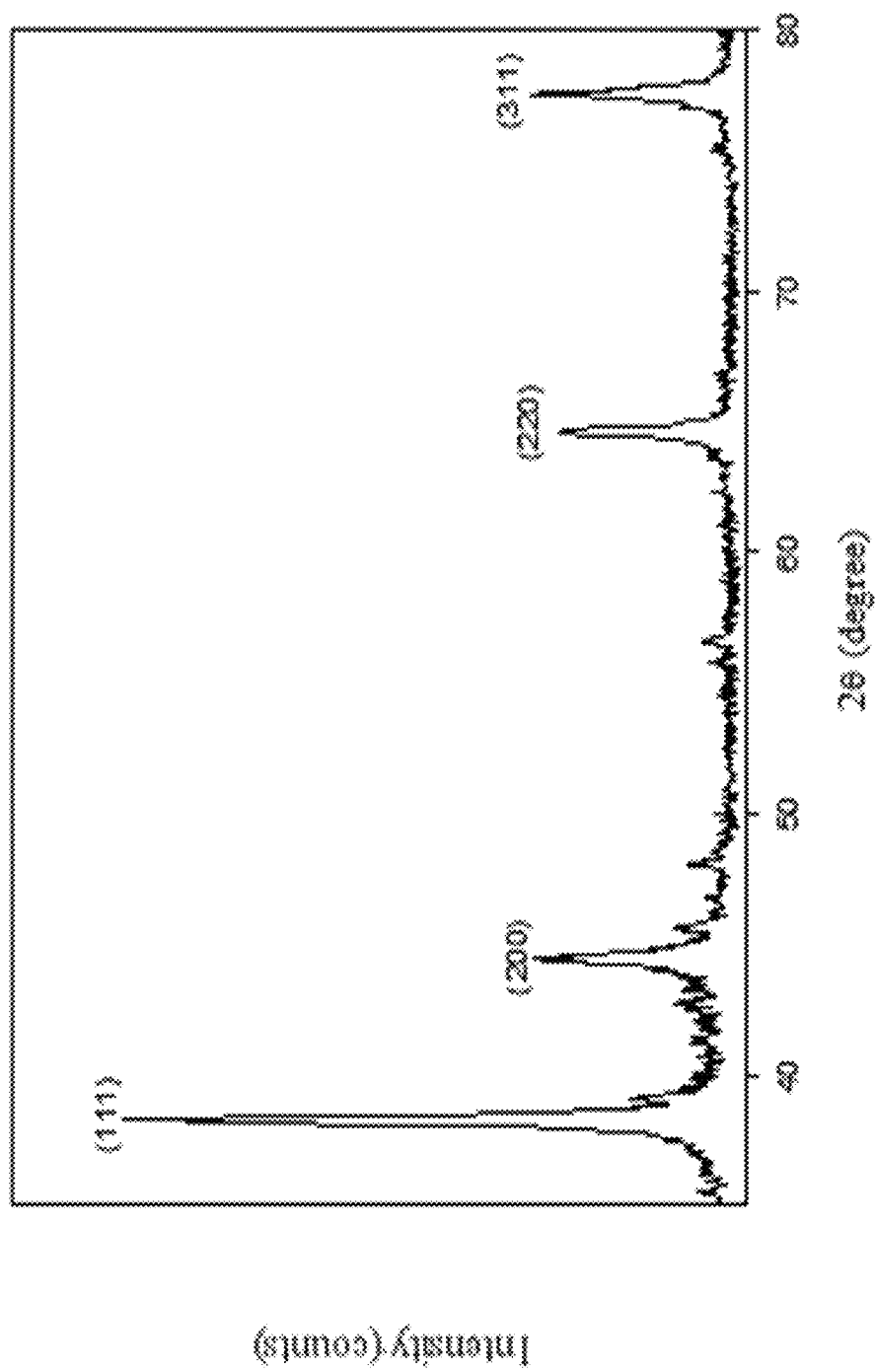
FIG. 12 is a graphical presentation of the XRD data of the biosynthesized silver nanoparticles according to Example 4.

The XRD pattern of the biosynthesized AgNPs is shown in FIG. 12, with the 4 peak X-ray diffractions indexed to 111, 200, 220 and 311 planes of the face-centered cubic (fcc) structure of silver according to JCPDS file No. 00-004-0783.

EXAMPLE 5

Figure 13:
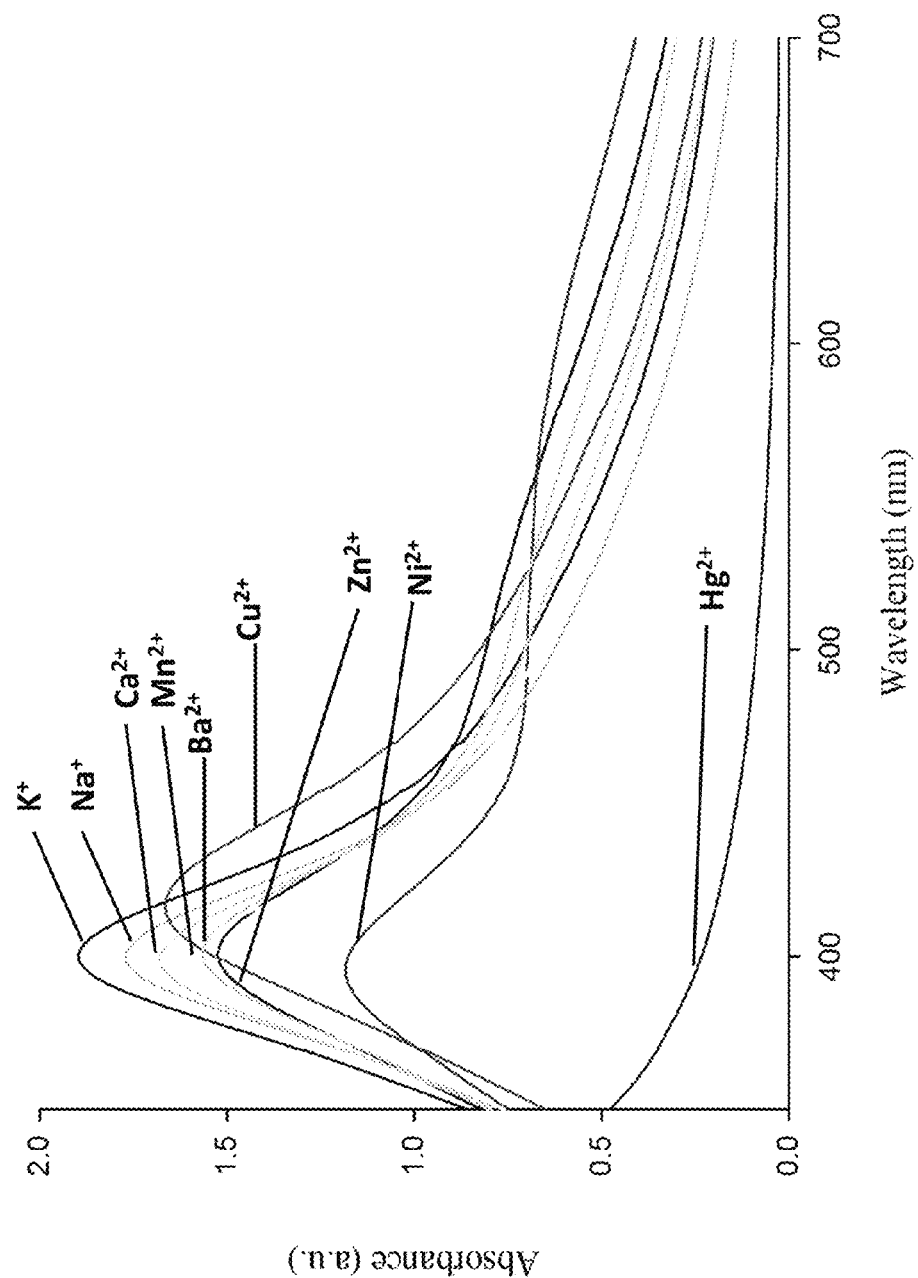
FIG. 13 is a graphical presentation of the UV-visible spectra of the aqueous mixtures containing the biosynthesized silver nanoparticles and one of the indicated metal cations according to Example 5.
Figure 14:
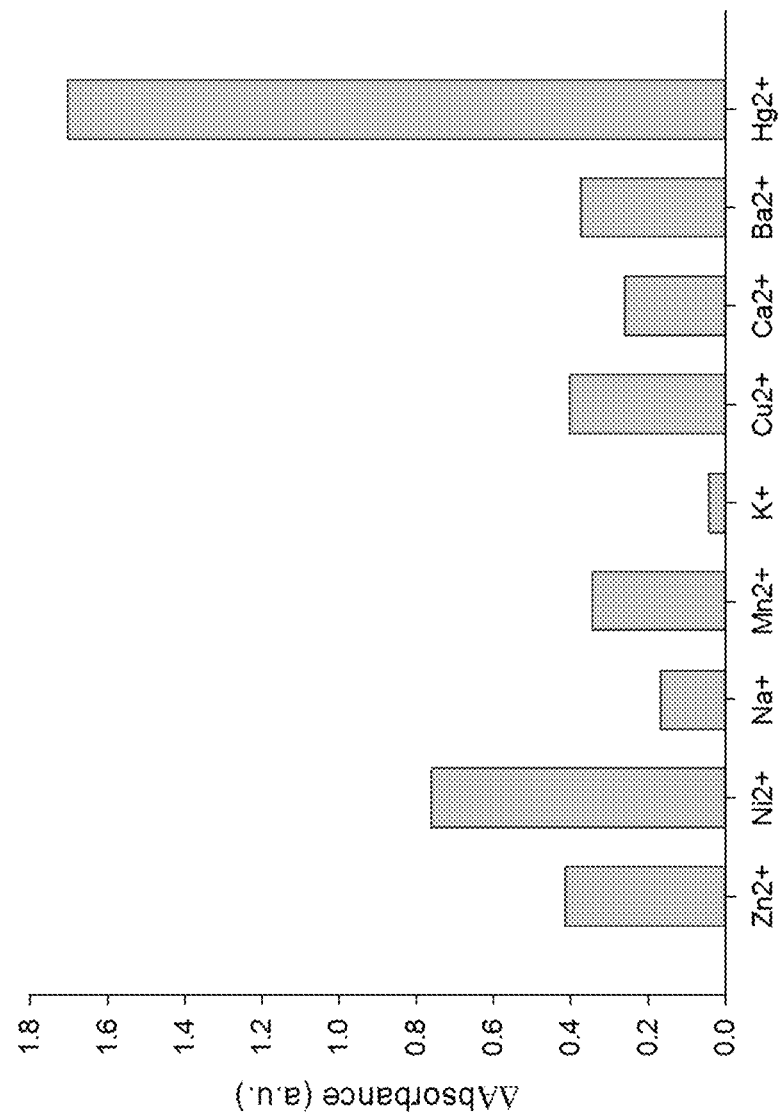
FIG. 14 is a graphical presentation of the changes in absorbance at the wavelength of 400 nm of the aqueous mixtures containing the biosynthesized silver nanoparticles and one of the indicated metal cations according to Example 5.

Sensitivity and Selectivity of the Biosynthesized Silver Nanoparticles in Detecting $Hg^{2+}$ in an Aqueous Solution After the addition of 1 ml of biosynthesized AgNPs to 9 ml of a colorless aqueous solution containing 1 mM $Hg^{2+}$, the resulting mixture initially had a golden brown color, which gradually changed to light brown and finally to colorless within 5 min. The change in color of the mixture indicated that the $Hg^{2+}$ had a large effect on the surface plasmon resonance vibration of the biosynthesized AgNPs. By contrast, when 1 ml of biosynthesized silver nanoparticles was added to 9 ml of an aqueous solution containing 1 mM of $Ca^{2+}$, $Cu^{2+}$, $Mn^{2+}$, $Ni^{2+}$, $Na^+$, $Zn^{2+}$, $Ba^{2+}$, or $K^+$, none of the resulting mixtures showed any color change, even after 15 min of mixing. FIG. 13 shows the UV-visible spectra of all the metal cation-biosynthesized silver nanoparticle mixtures. As shown in FIG. 14, the $Hg^{2+}$-biosynthesized silver nanoparticle mixture exhibited the largest change in absorbance among all the metal cation-biosynthesized silver nanoparticle mixtures studied. The change in absorbance ($\Delta$ absorbance) was the difference in absorbance between the metal cation containing aqueous solution-biosynthesized silver nanoparticle mixture and the blank control which was a mixture of 1 ml of biosynthesized silver nanoparticles and 9 ml of deionized water.

Figure 15:
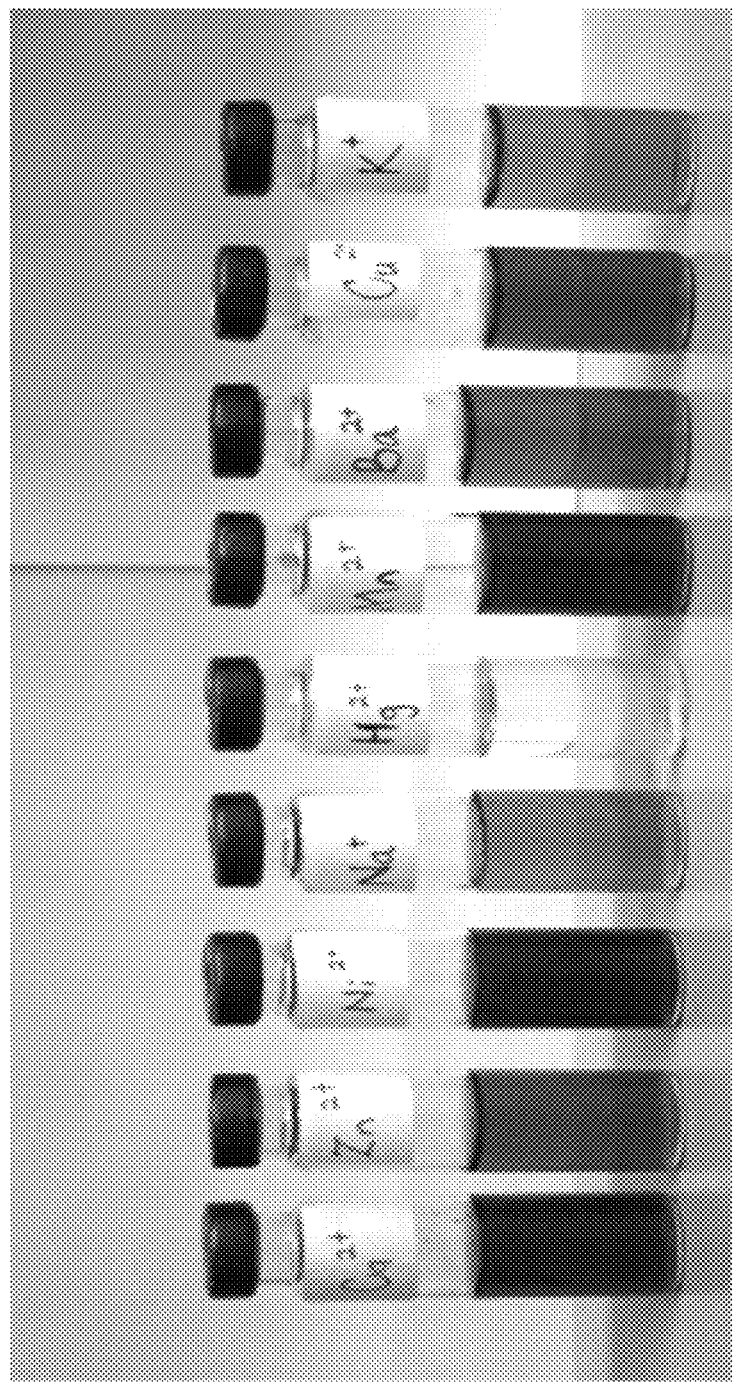
FIG. 15 is a picture showing the colors of the aqueous mixtures containing the biosynthesized silver nanoparticles and one of the indicated metal cations according to Example 5.

Referring to FIG. 13, the mixture of the $Hg^{2+}$ containing aqueous solution and the biosynthesized silver nanoparticles lacked a peak at a wavelength around 400 nm, whereas the mixture of the solution containing each of all the other metal cations and the biosynthesized silver nanoparticles as well as the blank control had a broad peak at or near the wavelength of 400 nm, confirming that the biosynthesized AgNPs could selectively and colorimetrically detect $Hg^{2+}$ in an aqueous solution. Referring to FIG. 15, the change in color of the mixture of the $Hg^{2+}$ containing aqueous solution and the biosynthesized silver nanoparticles, and the lack of such a color change when the $Hg^{2+}$ cation was replaced by the other metal ions, again confirmed the selectivity of the biosynthesized AgNPs for mercury (II) detection.

Figure 16:
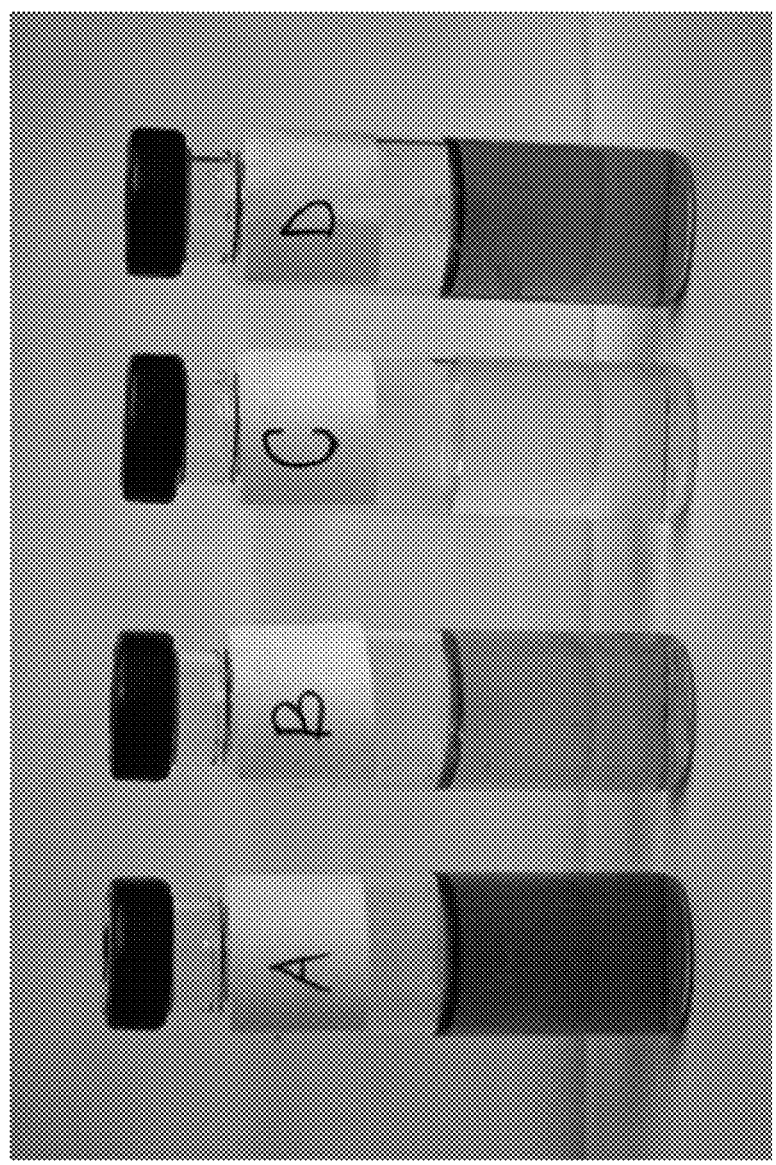
FIG. 16 is a picture showing the colors of the aqueous mixtures containing the biosynthesized silver nanoparticles and one of the following: mixed metal cations except $Hg^{2+}$ in Sample A; mixed metal cations including $Hg^{2+}$ in Sample B; $Hg^{2+}$ only in Sample C; or deionized water with no metal cation in Sample D according to Example 5.

Referring to FIG. 16, to further test the selectivity of the disclosed $Hg^{2+}$ detection method, an aqueous solution containing mixed metal cations was prepared by mixing equal volumes of 1 mM solutions of $CaCl_2$, $CuSO_4$, $MnSO_4$, $NiCl_2$, NaCl, $Zn(NO_3)_2$, $BaCl_2$, KCl, and $HgCl_2$. Then, 1 mL of biosynthesized AgNPs was added to 9 mL of the mixed metal cation aqueous solution to form a test mixture labeled as Sample B. For comparison, a mixed metal cation aqueous solution without $HgCl_2$ was similarly made by substituting the 1 mM $HgCl_2$ solution with the same volume of deionized water, and 9 ml of the mixed metal cation aqueous solution without $HgCl_2$ were likewise mixed with 1 ml of the biosynthesized silver nanoparticles to form another test mixture labeled as Sample A. Another comparison test mixture, labeled as Sample C, was a mixture of 9 ml of an aqueous solution containing $HgCl_2$ only, which was prepared by substituting each of the 1 mM non-$HgCl_2$ solutions with the same volume of deionized water, and 1 ml of the biosynthesized silver nanoparticles. Still another comparison test mixture, labeled as Sample D, was the blank control, which was a mixture of 9 ml of deionized water and 1 ml of the biosynthesized silver nanoparticles. Compared to Sample D (the blank control), Sample C displayed the strongest color change, whereas Sample A displayed the least color change, and Sample B displayed an intermediate color change.

Figure 17:
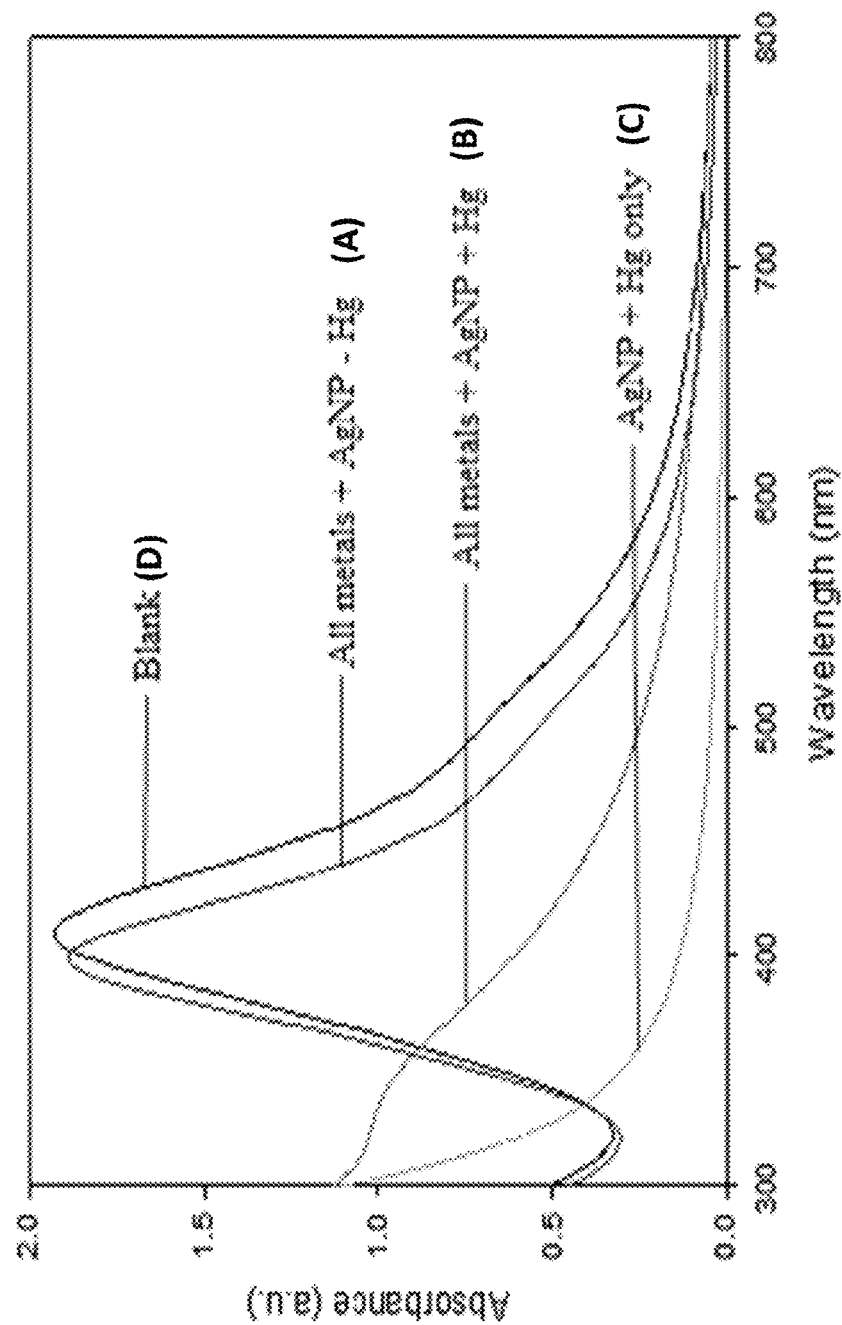
FIG. 17 is a graphical presentation of the UV-visible spectra of the aqueous mixtures of Samples A, B, C, and D described in FIG. 16 according to Example 5.

Referring to FIG. 17 showing the UV-visible spectrophotometry data of Samples A, B, C, and D, the presence of the other metal cations had very little interference with the detection of $Hg^{2+}$ in the aqueous solution. Contacting the biosynthesized silver nanoparticles with the aqueous solution containing $Hg^{2+}$ only in Sample C resulted in a colorless mixture with the largest change in color and absorbance as compared to the blank control (Sample D). By contrast, contacting the biosynthesized silver nanoparticles with the mixed metal cation aqueous solution without $Hg^{2+}$ in Sample A had almost the same color and absorbance as the blank control sample (Sample D). Contacting the biosynthesized silver nanoparticles with the aqueous solution containing all the mixed metal cations, including $Hg^{2+}$, in Sample B resulted in a partial change in color and absorbance as compared to Sample C and the blank control (Sample D).

Figure 18:
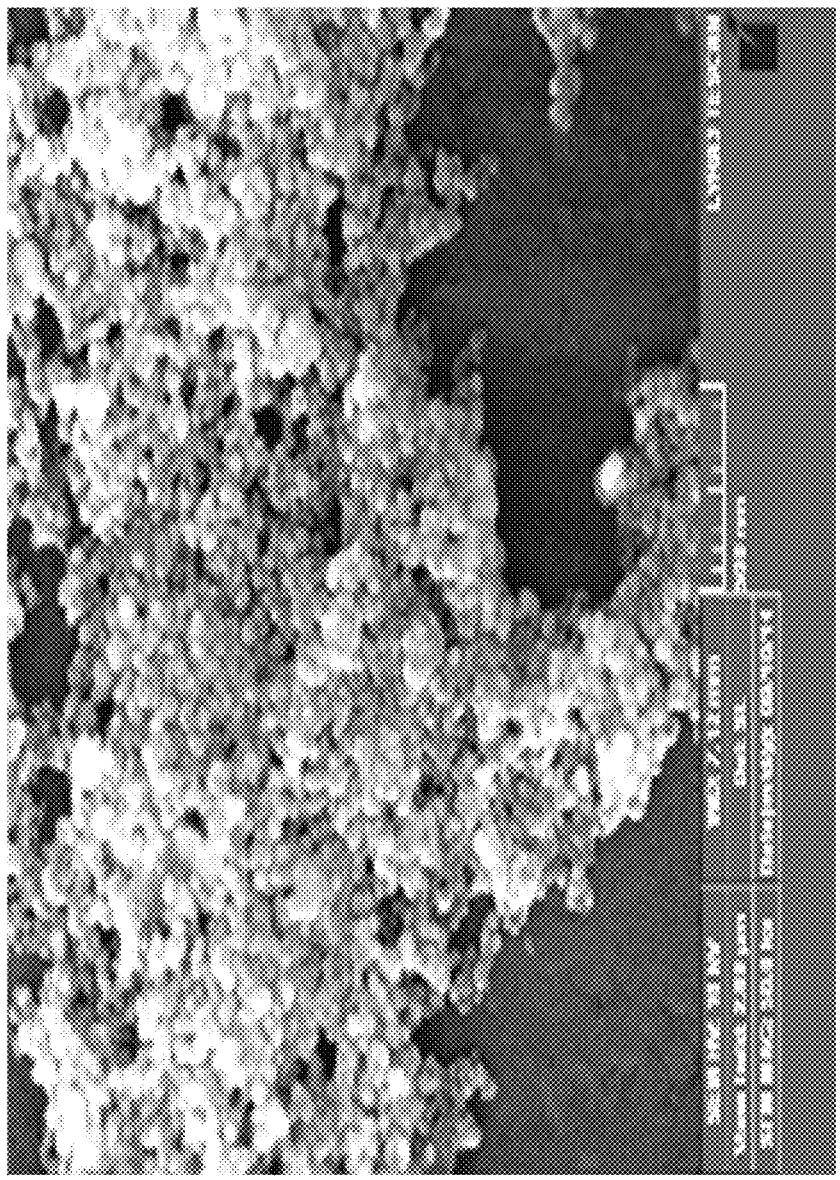
FIG. 18 is an SEM image of the biosynthesized silver nanoparticles prior to contacting $Hg^{2+}$ in an aqueous solution according to Example 5.
Figure 19:
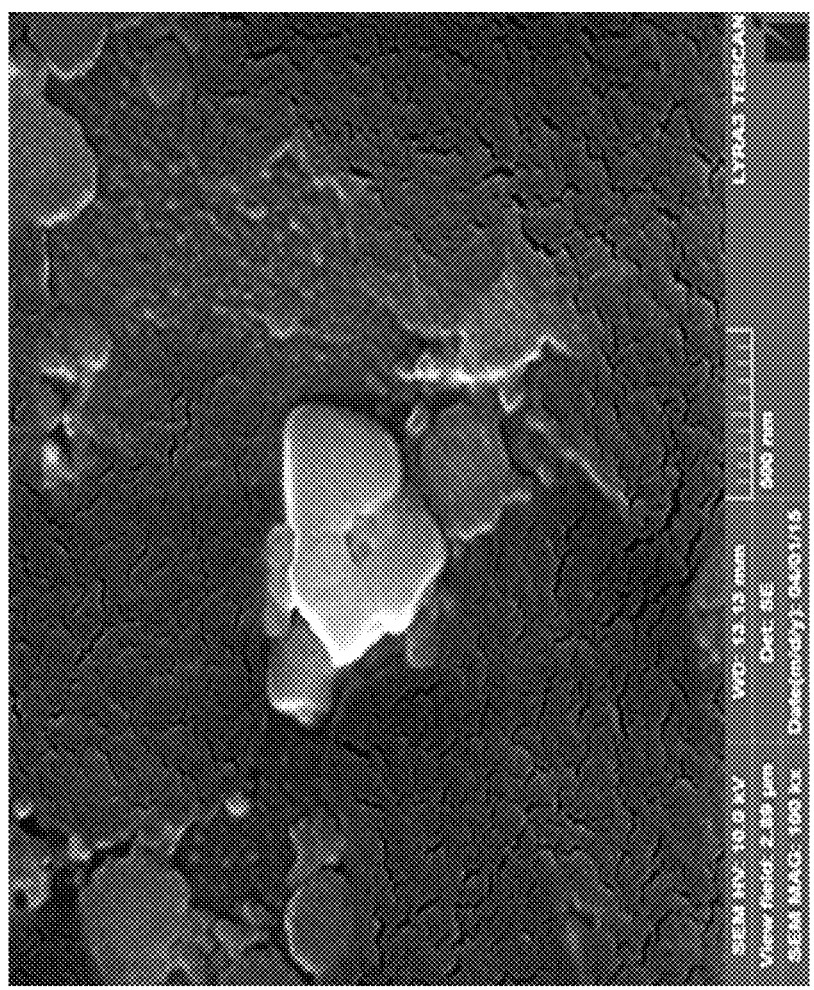
FIG. 19 is an SEM image of the biosynthesized silver nanoparticles after contacting $Hg^{2+}$ in an aqueous solution according to Example 5.

The selectivity of the biosynthesized silver nanoparticles for $Hg^{2+}$ detection occurred likely because the biosynthesized AgNPs and the $Hg^{2+}$ form a silver-mercury amalgam, where the $Hg^{2+}$ ion is reduced to metallic mercury. Scanning electron microscopy (SEM) images of the biosynthesized AgNPs before and after contacting $Hg^{2+}$ are shown in FIG. 18 and FIG. 19, respectively. Referring to FIG. 18, before contacting $Hg^{2+}$ in an aqueous solution, the biosynthesized silver nanoparticles were spherical-shaped and agglomerated. Referring to FIG. 19, by comparison, after the biosynthesized silver nanoparticles contacted $Hg^{2+}$ in an aqueous solution, there was a change in the surface morphology of the biosynthesized AgNPs and a reduction in the amount of the biosynthesized AgNPs.

Figure 20:
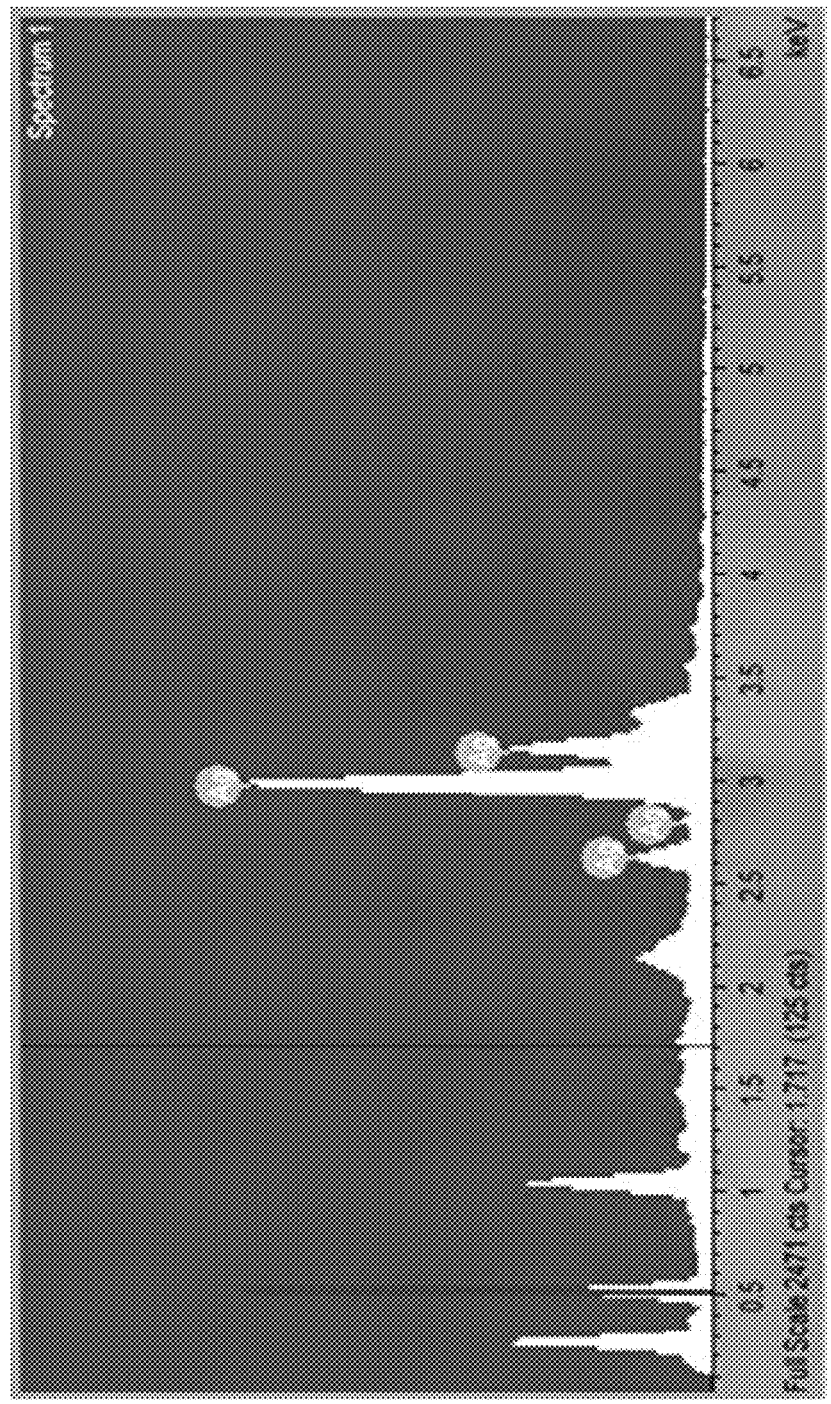
FIG. 20 is a graphical presentation of the EDS analysis data of the biosynthesized silver nanoparticles before contacting $Hg^{2+}$ in an aqueous solution according to Example 5.
Figure 21:
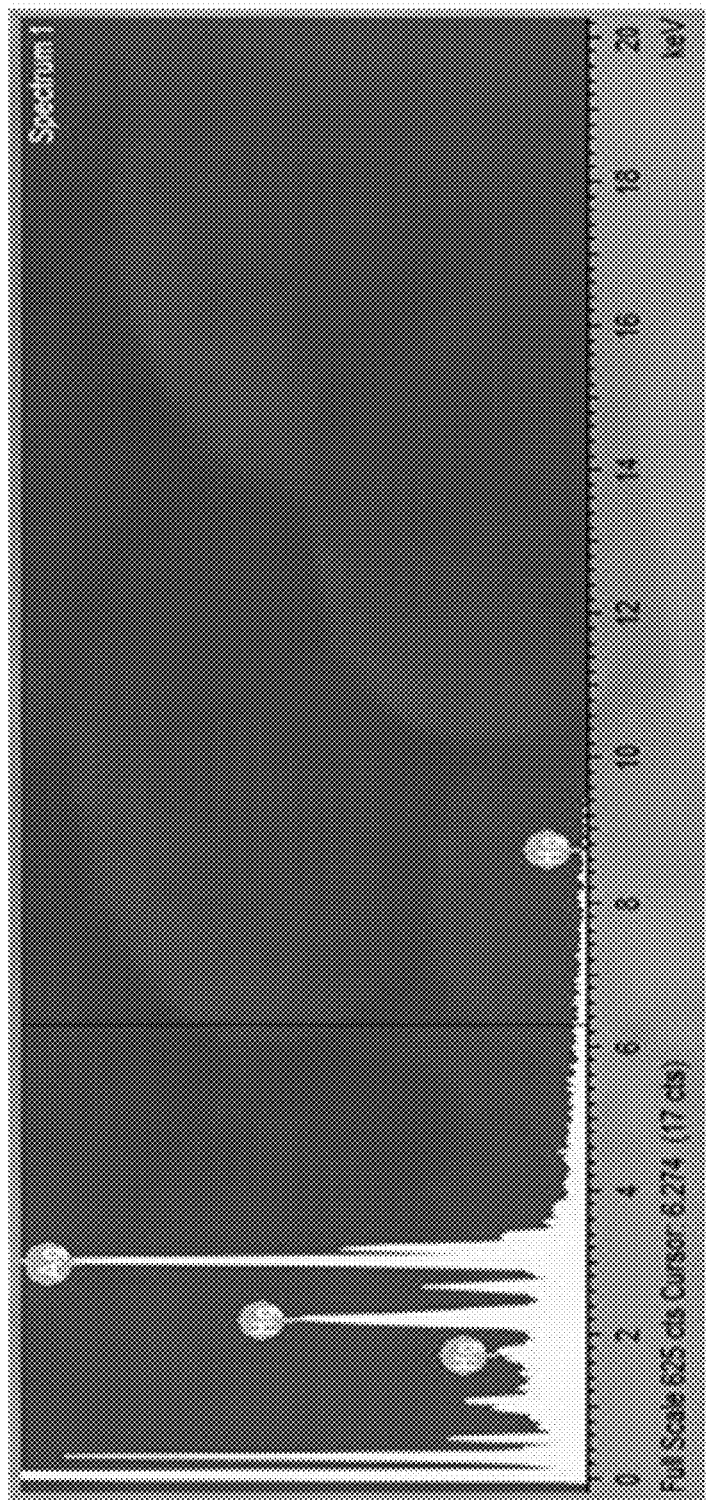
FIG. 21 is a graphical presentation of the EDS analysis data of the biosynthesized silver nanoparticles after contacting $Hg^{2+}$ in an aqueous solution according to Example 5.

FIG. 20 and FIG. 21 are EDS data of the biosynthesized silver nanoparticles before and after contacting $Hg^{2+}$ in an aqueous solution, respectively. Referring to FIG. 20, before contacting $Hg^{2+}$ in an aqueous solution, the biosynthesized silver nanoparticles mainly comprised silver. Referring to FIG. 21, by contrast, after contacting $Hg^{2+}$ in the aqueous solution, the biosynthesized silver nanoparticles contained both silver and metallic mercury.

Figure 22:
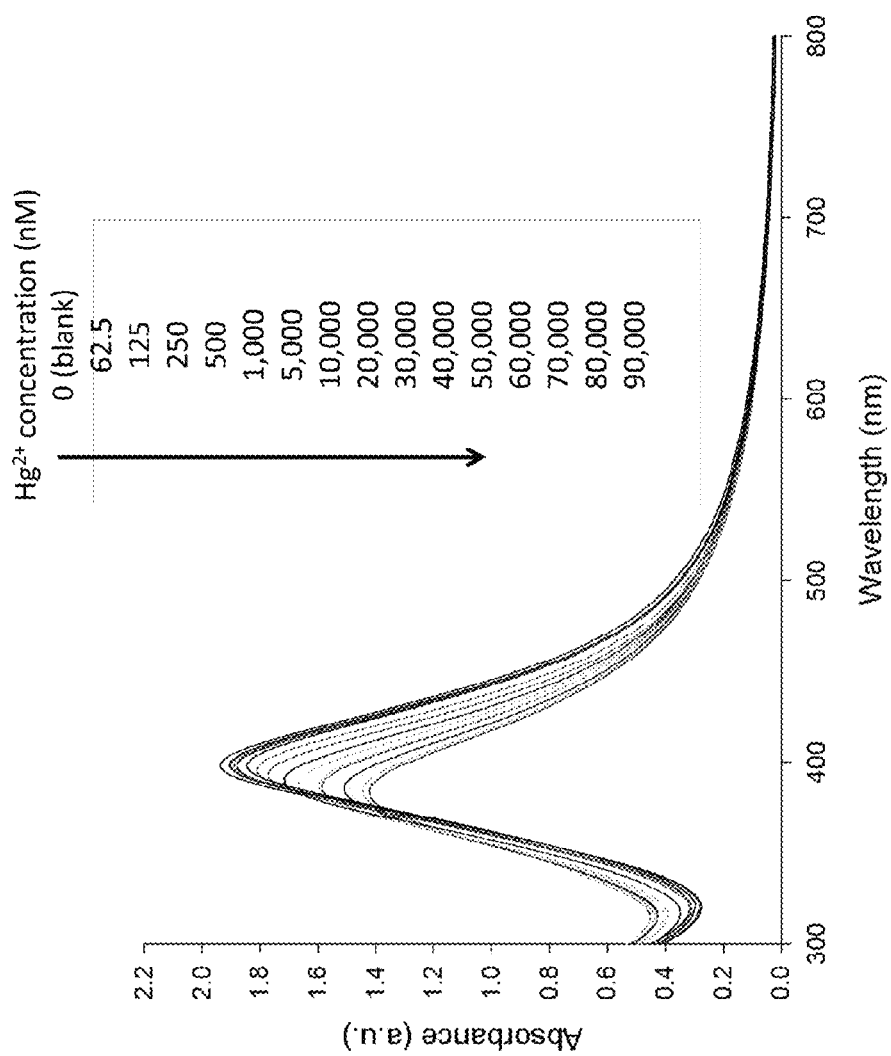
FIG. 22 is a graphical presentation of the UV-visible spectra of the aqueous mixtures prepared by adding the biosynthesized silver nanoparticles to a series of aqueous solutions containing $Hg^{2+}$ at the indicated concentrations according to Example 5.
Figure 23:
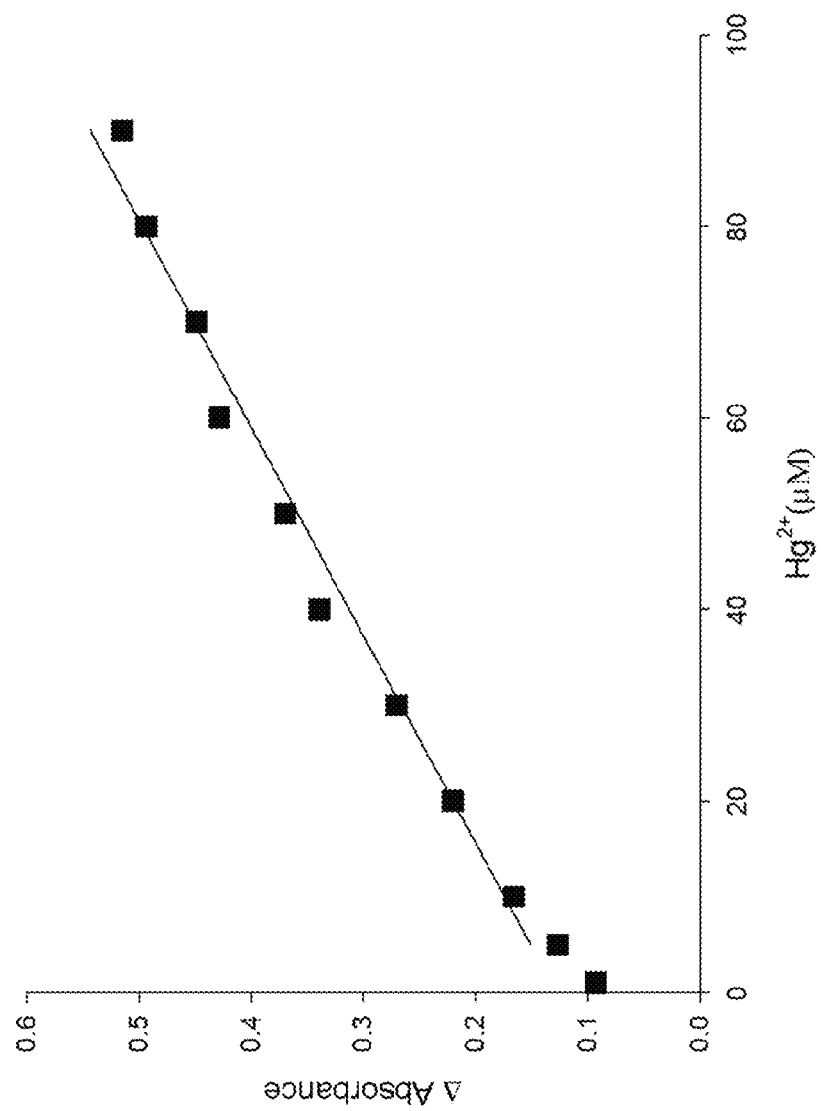
FIG. 23 is a graphical presentation of the linear relationship between the magnitude of the change in absorbance at the wavelength of 400 nm of the aqueous mixture prepared by adding the biosynthesized silver nanoparticles to a $Hg^{2+}$ containing aqueous solution and the $Hg^{2+}$ concentration in the $Hg^{2+}$ containing aqueous solution in the μM range according to Example 5.
Figure 24:
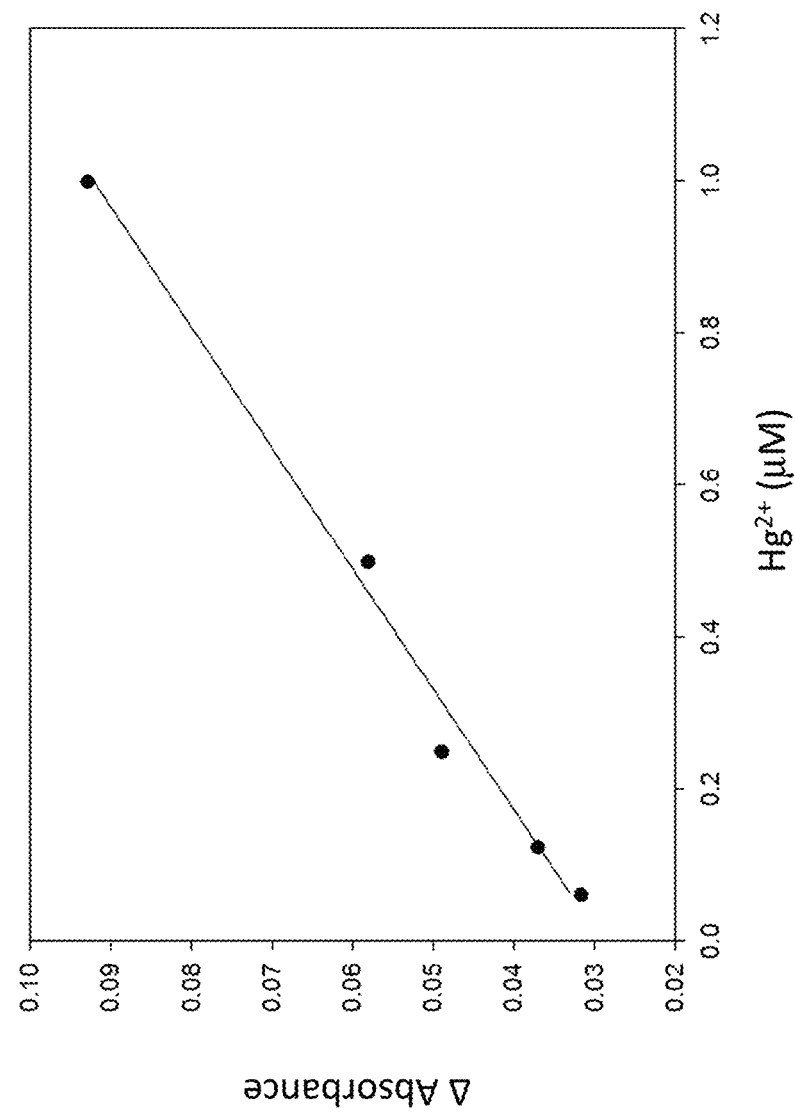
FIG. 24 is a graphical presentation of the linear relationship between the magnitude of the change in absorbance at the wavelength of 400 nm of the aqueous mixture prepared by adding the biosynthesized silver nanoparticles to a $Hg^{2+}$ containing aqueous solution and the $Hg^{2+}$ concentration in the $Hg^{2+}$ containing aqueous solution in the nM range according to Example 5.

In order to determine the sensitivity of the biosynthesized AgNPs for $Hg^{2+}$ detection, i.e. the detection limit of $Hg^{2+}$ in an aqueous solution, a series of $Hg^{2+}$ containing aqueous solutions was made, with the $Hg^{2+}$ concentration reduced progressively from 90 μM to 62.5 nM. 9 ml of each of the $Hg^{2+}$ containing solutions were mixed with 1 ml of the biosynthesized silver nanoparticles under the same conditions. With decreasing $Hg^{2+}$ concentrations in the mixture, the intensity of the color change decreased; however, the UV-visible spectrophotometry was able to detect a change in absorbance at the wavelength of 400 nm between each of the $Hg^{2+}$ containing aqueous solution-biosynthesized silver nanoparticle mixtures and the blank control shown in FIG. 22. The blank control contained 0 nM $Hg^{2+}$ and was a mixture of 9 ml of deionized water and 1 ml of the biosynthesized silver nanoparticles. Additionally, the magnitude of the change in absorbance detected by the UV-visible spectrophotometry linearly correlated with the $Hg^{2+}$ concentration in the $Hg^{2+}$ containing aqueous solution ranging from 1 μM to 90 μM shown in FIG. 23, with the linear regression value of 0.98. Further, a linear relationship between the magnitude of the change in absorbance detected by the UV-visible spectrophotometry and the $Hg^{2+}$ concentration in the $Hg^{2+}$ containing aqueous solution was also present when the $Hg^{2+}$ concentration in the $Hg^{2+}$ containing aqueous solution was below 1 μM in the nM range shown in FIG. 24, with the linear regression value being 0.98 as well.

The invention claimed is:

1. A method of detecting $Hg^{2+}$ in an aqueous solution, comprising:
   contacting the aqueous solution with a composition comprising an extract of a leaf and/or a flower from at least one species of *Ocimum* genus and biosynthesized silver nanoparticles,
   wherein the biosynthesized silver nanoparticles are agglomerated, and detecting and quantifying a color change following the contacting that indicates the presence and a concentration of $Hg^{2+}$ in the aqueous solution, wherein the detected and quantified color change correlates with the concentration of $Hg^{2+}$ in the aqueous solution, and a lowest concentration of Hg2+ in the aqueous solution that is detectable by the color change is from 40 to 200 nM.

2. The method of claim 1, wherein the biosynthesized silver nanoparticles are of uniform shape.

3. The method of claim 2, wherein the uniform shape is selected from the group consisting of a spherical shape, a triangular shape, a rod shape, and a cubic shape.

4. The method of claim 1, wherein the color change is detected and quantified by a decrease in absorbance at a wavelength of from 380 to 450 nm by UV-visible spectrophotometry.

5. The method of claim 4, wherein a magnitude of the color change detected by the UV-visible spectrophotometry linearly correlates with the concentration of $Hg^{2+}$ in the aqueous solution in a range of from about 1 µM to 90 µM.

6. The method of claim 1, wherein the aqueous solution further comprises at least one metal cation selected from of the group consisting of $Ca^{2+}$, $Cu^{2+}$, $Mn^{2+}$, $Ni^{2+}$, $Na^+$, $Zn^{2+}$, $Ba^{2+}$, and $K^+$.

7. The method of claim 1, wherein the at least one species of the *Ocimum* genus is selected from the group consisting of *Ocimum basilicum, Ocimum africanum, Ocimum americanum, Ocimum amicorum, Ocimum angustifolium, Ocimum burchellianum, Ocimum campechianum, Ocimum canescens, Ocimum carnosum, Ocimum centraliafricanum, Ocimum circinatum, Ocimum coddii, Ocimum cufodontii, Ocimum dambicola, Ocimum decumbens, Ocimum dhofarense, Ocimum dolomiticola, Ocimum ellenbeckii, Ocimum empetroides, Ocimum ericoides, Ocimum filamentosum, Ocimum fimbriatum, Ocimum fischeri, Ocimum formosum, Ocimum forskoelei, Ocimum fruticosum, Ocimum grandiflorum, Ocimum gratissimum, Ocimum hirsutissimum, Ocimum irvinei, Ocimum jamesii, Ocimum kenyense, Ocimum kilimandscharicum, Ocimum labiatum, Ocimum lamiifolium, Ocimum masaiense, Ocimum mearnsii, Ocimum metallorum, Ocimum minimum, Ocimum minutiflorum, Ocimum mitwabense, Ocimum monocotyloides, Ocimum motjaneanum, Ocimum natalense, Ocimum nudicaule, Ocimum nummularia, Ocimum obovatum, Ocimum ovatum, Ocimum pseudoserratum, Ocimum pyramidatum, Ocimum reclinatum, Ocimum serpyllifolium, Ocimum serratum, Ocimum somaliense, Ocimum spectabile, Ocimum spicatum, Ocimum tenuiflorum, Ocimum transamazonicum, Ocimum tubiforme, Ocimum urundense, Ocimum vandenbrandei, Ocimum vanderystii, Ocimum viphyense*, and *Ocimum waterbergense*.

8. The method of claim 7, wherein the composition is synthesized by reduction of a silver salt with the extract of the leaf and/or the flower from *Ocimum basilicum*.

9. The method of claim 8, wherein the reduction of the silver salt with the extract of the leaf and/or the flower from *Ocimum basilicum* comprises mixing an aqueous solution of the silver salt with an aqueous extract of the leaf and/or the flower from *Ocimum basilicum* and reducing the silver salt with the aqueous extract of the leaf and/or the flower from *Ocimum basilicum* for a period of at least 120 minutes to form a biosynthesized silver nanoparticle mixture.

10. The method of claim 8, wherein the reduction of the silver salt with the extract of the leaf and/or the flower from *Ocimum basilicum* comprises mixing an aqueous solution of the silver salt with an aqueous extract of the leaf and/or the flower from *Ocimum basilicum* and reducing the silver salt with the aqueous extract of the leaf and/or the flower from *Ocimum basilicum* in a temperature range of from 20 to 75° C. to form a biosynthesized silver nanoparticle mixture.

11. The method of claim 8, wherein the reduction of the silver salt with the extract of the leaf and/or the flower from *Ocimum basilicum* comprises mixing an aqueous solution of the silver salt with an aqueous extract of the leaf and/or the flower from *Ocimum basilicum* to form a reaction mixture with a pH of from 7 to 12 and reducing the silver salt with the aqueous extract of the leaf and/or the flower from *Ocimum basilicum* to form a biosynthesized silver nanoparticle mixture.

12. The method of claim 8, wherein the reduction of the silver salt with the extract of the leaf and/or the flower from *Ocimum basilicum* comprises mixing an aqueous solution of the silver salt with an aqueous extract of the leaf and/or the flower from *Ocimum basilicum* and reducing the silver salt with the aqueous extract of the leaf and/or the flower from *Ocimum basilicum* to form a biosynthesized silver nanoparticle mixture,
wherein a concentration of the silver salt in the aqueous solution of the silver salt is from 1 to 5 mM, and
wherein a volume ratio of the aqueous extract of the leaf and/or the flower from *Ocimum basilicum* to the aqueous solution of the silver salt is no greater than 1:1.

13. The method of claim 8, wherein the reduction of the silver salt with the extract of the leaf and/or the flower from *Ocimum basilicum* comprises mixing an aqueous solution of the silver salt with an aqueous extract of the leaf and/or the flower from *Ocimum basilicum* and reducing the silver salt with an effective amount of the aqueous extract of the leaf and/or the flower from *Ocimum basilicum* to form a biosynthesized silver nanoparticle mixture,
wherein the aqueous extract of the leaf and/or the flower from *Ocimum basilicum* is produced by boiling at least one leaf, or a part thereof, and/or at least one flower, or a part thereof of *Ocimum basilicum* in water, and
wherein a ratio of a weight of the at least one leaf, or a part thereof, and/or the at least one flower, or a part thereof of *Ocimum basilicum* to a volume of the water is about 3-30 g of the at least one leaf, or a part thereof, and/or the at least one flower, or a part thereof of *Ocimum basilicum* per 100 ml of the water.

14. The method of claim 13, wherein the effective amount of the aqueous extract of the leaf and/or the flower from *Ocimum basilicum* corresponds to a volume ratio of the aqueous extract of the leaf and/or the flower from *Ocimum basilicum* to the aqueous solution of the silver salt in a range of from 1:20 to 1:75.

15. The method of claim 8, wherein the silver salt comprises at least one selected from the group consisting of silver halide, silver sulfate, and silver nitrate.

16. The method of claim 8, wherein the reduction of a silver salt with an extract of the leaf and/or the flower from *Ocimum basilicum* comprises mixing an aqueous solution of the silver salt with an aqueous extract of the leaf and/or the flower from *Ocimum basilicum* to form a reaction mixture with a pH of from 9 to 11 and reducing the silver salt with the aqueous extract of the leaf and/or the flower from *Ocimum basilicum* for a duration from 120 to 240 minutes and at a temperature of from 20 to 75° C. to form a biosynthesized silver nanoparticle mixture,
wherein a concentration of the silver salt in the aqueous solution of the silver salt is about 1-3 mM, and wherein a volume ratio of the aqueous extract of *Ocimum basilicum* to the aqueous solution of the silver salt is in a range of from 1:20 to 1:75.

17. The method of claim 16, further comprising separating the composition from the biosynthesized silver nanoparticle mixture.

18. The method of claim 8, wherein the reduction of the silver salt with the extract of *Ocimum basilicum* comprises mixing an aqueous solution of the silver salt with an aqueous extract of *Ocimum basilicum* to form a reaction mixture and reducing the silver salt with the aqueous extract of *Ocimum basilicum* to form a biosynthesized silver nanoparticle mixture, wherein an average particle size and shape of the composition are determined by a pH of the reaction mixture, a duration and a temperature of the reducing, a concentration of the silver salt and a concentration of the aqueous extract of *Ocimum basilicum* in the reaction mixture, a part of *Ocimum basilicum* used to make the aqueous extract of *Ocimum basilicum*, and a type of *Ocimum basilicum* used.

19. The method of claim 1, further comprising suspending an appropriate amount of the composition in water thereby forming a suspension; and centrifuging the suspension thereby making the composition into a form of pellet, before contacting the aqueous solution with the composition.

20. The method of claim 1, wherein the lowest concentration of $Hg^{2+}$ in the aqueous solution is in a range of from 50 to 100 nM.

* * * * *